United States Patent
Iino et al.

(10) Patent No.: US 12,411,146 B2
(45) Date of Patent: Sep. 9, 2025

(54) METHOD FOR MEASURING AMYLOID β PEPTIDE

(71) Applicant: SYSMEX CORPORATION, Kobe (JP)

(72) Inventors: Takuya Iino, Kobe (JP); Shunsuke Watanabe, Kobe (JP); Kouzou Suto, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 241 days.

(21) Appl. No.: 17/357,209

(22) Filed: Jun. 24, 2021

(65) Prior Publication Data
US 2021/0405068 A1 Dec. 30, 2021

(30) Foreign Application Priority Data
Jun. 25, 2020 (JP) ................................ 2020-109825

(51) Int. Cl.
*G01N 33/68* (2006.01)

(52) U.S. Cl.
CPC . *G01N 33/6896* (2013.01); *G01N 2800/2821* (2013.01)

(58) Field of Classification Search
CPC ....... G01N 33/6896; G01N 2800/2821; G01N 33/6848; G01N 33/6851; G01N 30/02; G01N 30/06; G01N 30/72; G01N 30/74
See application file for complete search history.

(56) References Cited

U.S. PATENT DOCUMENTS

| | | | | |
|---|---|---|---|---|
| 9,759,732 | B2 * | 9/2017 | Grabert | ............. G01N 33/6854 |
| 2010/0266596 | A1 | 10/2010 | Cox | |
| 2014/0051105 | A1 | 2/2014 | Vogelstein et al. | |
| 2016/0334420 | A1 | 11/2016 | Kaneko | |
| 2017/0016910 | A1 | 1/2017 | Kaneko | |

FOREIGN PATENT DOCUMENTS

| | | |
|---|---|---|
| CN | 102687020 A | 9/2012 |
| CN | 103547593 A | 1/2014 |
| CN | 108603880 A | 9/2018 |
| JP | 2011-507909 A | 3/2011 |
| JP | 2017-20980 A | 1/2017 |
| JP | 6129868 B2 | 5/2017 |
| JP | 2018-194374 A | 12/2018 |
| JP | 2018194374 * | 12/2018 |

(Continued)

OTHER PUBLICATIONS

Bros et al (Quantitative detection of amyloid-β peptides by mass spectrometry: state of the art and clinical applications, Clin Chem Lab Med 2015; 53(10): 1483-1493) (Year: 2015).*

(Continued)

*Primary Examiner* — Bao-Thuy L Nguyen
*Assistant Examiner* — Chau N. B. Tran
(74) *Attorney, Agent, or Firm* — Sughrue Mion, PLLC

(57) ABSTRACT

Disclosed is a method for measuring an Aβ peptide, comprising: mixing a blood sample comprising an Aβ peptide and an antibody that specifically binds to the Aβ peptide to form a complex of the Aβ peptide and the antibody; releasing the AP peptide from the complex with a basic solution comprising an organic solvent; and measuring the released Aβ peptide by mass spectrometry.

13 Claims, 15 Drawing Sheets

Specification includes a Sequence Listing.

(56) References Cited

FOREIGN PATENT DOCUMENTS

| | | |
|---|---|---|
| WO | 2008/065806 A1 | 6/2008 |
| WO | 2009/086277 A1 | 7/2009 |
| WO | 2015/191825 A1 | 12/2015 |

OTHER PUBLICATIONS

Biosensis (Amyloid beta peptide (A-beta 40/42), Mouse Monoclonal Antibody, 2016) (Year: 2016).*

Janeway et al. (Immunobiology: the Immune System in Health and Disease (2001), Elsevier Science Ltd/Garland Publishing, New York, NY, Fifth Edition, see sections 3-6 and 3-7) (Year: 2001).*

Almagro et al. ("Humanization of Antibodies", Frontiers in Bioscience 13, 1619-1633, 2008) (Year: 2008).*

Goel et al. ("Plasticity within the Antigen Combining Site May Manifest as Molecular Mimicry in the Humoral Immune Response", The Journal of Immunology 173(12):7358-7367, 2004) (Year: 2004).*

Edwards et al. ("The remarkable flexibility of the human antibody repertoire; isolation of over one thousand different antibodies to a single protein, BLyS" J. Mol. Biol. (2003) 334, 103-118, DOI: 10.1016/j.jmb.2003.09.054) (Year: 2003).*

Lloyd et al. ("Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058) (Year: 2009).*

Brown et al. ("Tolerance of single, but not multiple, amino acid replacements in antibody VH CDR 2: a means of minimizing B cell wastage from somatic hypermutation?", J Immunol. May 1996;156(9):3285-91) (Year: 1996).*

Vajdos et al. ("Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4) (Year: 2002).*

Nakamura et al. (High performance plasma amyloid-beta biomarkers for Alzheimer's disease, Nature, vol. 554, No. 7691, pp. 249-254, 2018) (Year: 2018).*

Akinori Nakamura et al: "High performance plasma amyloid-β biomarkers for Alzheimer's disease", Nature, Jan. 31, 2018, vol. 554, No. 7691, pp. 249-254.

Thomas J. Esparza et al: "Soluble Amyloid-beta Aggregates from Human Alzheimer's Disease Brains", Scientific Reports, Dec. 5, 2016, vol. 6, No. 1, 16 pages in total.

Pauline Bros et al: "Quantitative detection of amyloid-β peptides by mass spectrometry: state of the art and clinical applications", Clinical Chemistry and Laboratory Medicine, Feb. 18, 2015, vol. 53, No. 10, pp. 1483-1493.

Takuya Iino et al: "Quantification of Amyloid—in Plasma by Simple and Highly Sensitive Immunoaffinity Enrichment and LC-MS/MS Assay", The Journal of Applied Laboratory Medicine, Jan. 19, 2021, vol. 6, No. 4, pp. 834-845.

Giuseppe Grasso: "The use of mass spectrometry to study amyloid-β peptides", Mass Spectrometry Reviews, Nov. 22, 2010, vol. 30, No. 3, pp. 347-365.

Extended European search report issued on Nov. 12, 2021 in a counterpart European patent application No. 21181621.0.

Andreas Leinenbach et al., "Mass Spectrometry-Based Candidate Reference Measurement Procedure for Quantification of Amyloid-β in Cerebrospinal Fluid", Clinical Chemistry, American Association for Clinical Chemistry, 2014, pp. 987-994, 60:7.

Sara Galozzi, "Development of Mass Spectrometry-based Identification and Quantification Methods for Protein Biomarkers in Alzheimer's and Parkinson's Diseases", Jul. 2016, 211 pages, Dissertation submitted to the Faculty of Chemistry and Biochemistry of the Ruhr-University Bochum, Germany.

Bio-Rad Laboratories, Inc., "Immunoaffinity Chromatography with Affinity Supports", Bulletin 1099, 1990, pp. 1-4, U.S.A.

Naoki Kaneko et al., "Identification and quantification of amyloid beta-related peptides in human plasma using matrix-assisted laser desorption/ionization time-of-flight mass spectrometry", Proceedings of the Japan Academy, Series B, 2014, pp. 104-117, vol. 90, No. 3.

Mary E. Lame et al., "Quantitation of amyloid beta peptides Aβ1-38, Aβ1-40, and Aβ1-42 in human cerebrospinal fluid by ultra-performance liquid chromatography-tandem mass spectrometry", Analytical Biochemistry, 2011, pp. 133-139, vol. 419, No. 2.

Thanh Duc Mai et al., "In-capillary immuno-preconcentration with circulating bio-functionalized magnetic beads for capillary electrophoresis", Analytica Chimica Acta, 2019, pp. 156-164, vol. 1062.

Romain Verpillot et al., "Analysis of Amyloid-β Peptides in Cerebrospinal Fluid Samples by Capillary Electrophoresis Coupled with LIF Detection", Analytical Chemistry, 2011, pp. 1696-1703, vol. 83.

Erin E. Chambers et al., "An Improved SPE/LC/MS/MS Platform for the Simultaneous Quantitation of Multiple Amyloid β Peptides in Cerebrospinal Fluid for Preclinical or Biomarker Discovery", Application Note, 2011, Waters Corporation.

Timothy M. Ryan et al., "Ammonium hydroxide treatment of Aβ produces an aggregate free solution suitable for biophysical and cell culture characterization", PeerJ, 2013, pp. 1-20, 1:e73.

Japanese Office Action issued on Jan. 23, 2024 in a counterpart Japanese patent application No. 2020-109825.

Nigel J. Clarke et al., "Detection and quantitation of cellularly derived amyloid β peptides by immunoprecipitation-HPLC-MS", FEBS Letters, 1998, pp. 419-423, No. 430.

Lieve Dillen et al., "A screening UHPLC-MS/MS method for the analysis of amyloid peptides in cerebrospinal fluid of preclinical species", Bioanalysis, 2011, pp. 45-55, No. 3, vol. 1.

Chinese Office Action issued on May 11, 2024 in a counterpart Chinese patent application No. 202110682916.X.

Chinese Office Action issued on Sep. 5, 2024 in a counterpart Chinese patent application No. 202110682916.X.

* cited by examiner

Aβ40 CALIBRATION CURVE

Aβ42 CALIBRATION CURVE

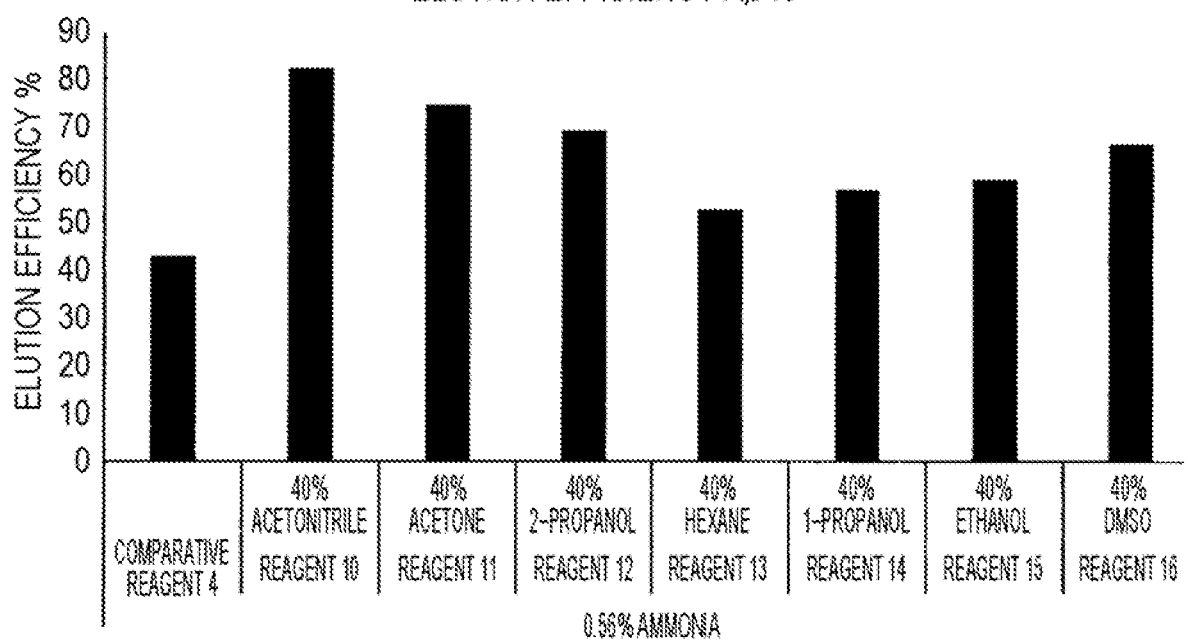
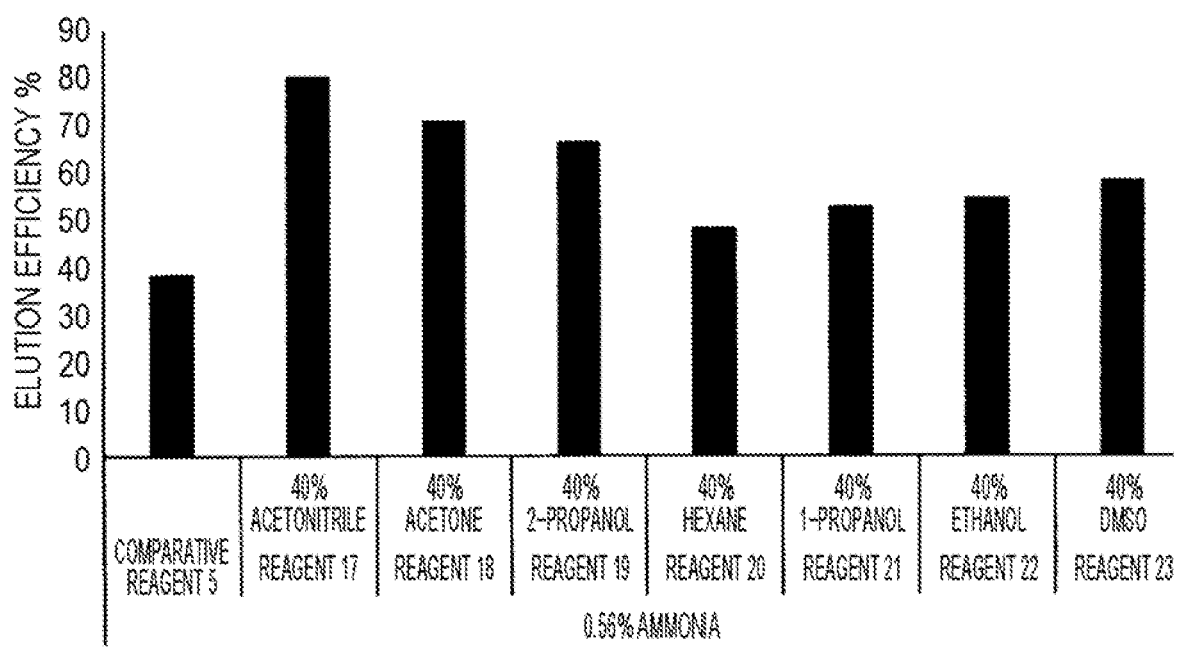

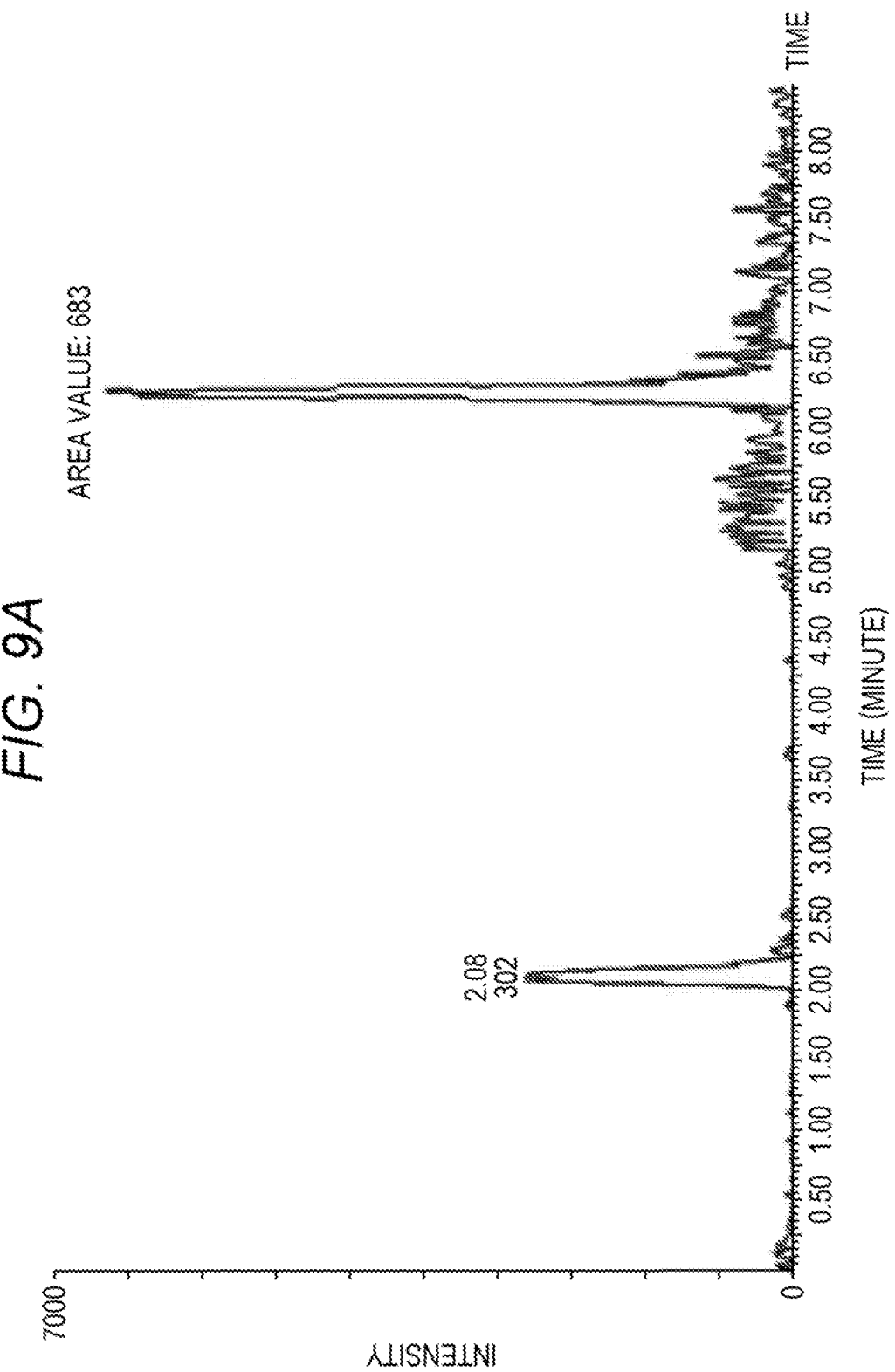

SEQUENCE LISTING

```
<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
            35                  40

<210> SEQ ID NO 2
<211> LENGTH: 42
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

METHOD FOR MEASURING AMYLOID β PEPTIDE

CROSS REFERENCE TO RELATED APPLICATIONS

This application claims priority from prior Japanese Patent Application No. 2020-109825, filed on Jun. 25, 2020, entitled "Method for measuring Aβ peptide and reagent composition used in the method", the entire contents of which are incorporated herein by reference.

FIELD OF THE INVENTION

The present invention relates to a method for measuring amyloid β (Aβ) peptide.

BACKGROUND

An Aβ peptide in a biological sample collected from a subject is known to be a biomarker for Alzheimer's disease. Since cerebrospinal fluid (CSF) contains a relatively large amount of Aβ peptide among biological samples, a method for quantitatively measuring an Aβ peptide in CSF has been established. For example, Leinenbach A. et al., Mass Spectrometry-Based Candidate Reference Measurement Procedure for Quantification of Amyloid-β in Cerebrospinal Fluid. Clinical Chemistry 60: 7 987-994 (2014) describes that an Aβ peptide in CSF is measured by liquid chromatography-mass spectrometry (LC-MS).

Since collection of CSF is invasive, burden on a subject is large. Therefore, recently, a method for measuring an Aβ peptide using blood, which has a low collection burden, as a biological sample has been developed. However, since the amount of Aβ peptide contained in blood is less than that in CSF, a method for accurately measuring an Aβ peptide has been required. An object of the present invention is to provide a means for enabling accurate measurement of Aβ peptide in blood.

SUMMARY OF THE INVENTION

The scope of the present invention is defined solely by the appended claims, and is not affected to any degree by the statements within this summary.

The present invention provides a method for measuring an Aβ peptide, comprising mixing i) a blood sample containing an Aβ peptide and ii) an antibody that specifically binds to the Aβ peptide, to form a complex of the Aβ peptide and the antibody, releasing the Aβ peptide from the complex with a basic solution containing an organic solvent, and measuring the released Aβ peptide by mass spectrometry.

BRIEF DESCRIPTION OF THE DRAWINGS

FIG. 6A is a diagram showing difference in elution efficiency of Aβ40 peptide due to a difference in organic solvent of free reagent;

FIG. 6B is a diagram showing difference in elution efficiency of Aβ42 peptide due to a difference in organic solvent of free reagent;

FIG. 9A is a diagram showing an amount of Aβ40 peptide when a 50 pg/ml Aβ40 peptide solution is eluted with a basic solution;

DETAILED DESCRIPTION OF THE PREFERRED EMBODIMENTS

Figure 1:
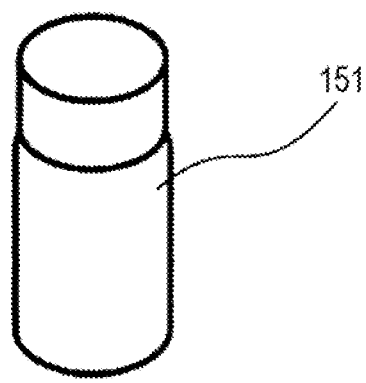
FIG. 1 is a diagram showing an example of a container containing a reagent composition.

The method for measuring an Aβ peptide of the present embodiment is a method for measuring an Aβ peptide captured by an antibody by mass spectrometry (hereinafter, also referred to as "measurement method"). This measurement method is characterized in that the Aβ peptide is released from the complex of the Aβ peptide and the antibody with a basic solution containing an organic solvent, and the released Aβ peptide is measured by mass spectrometry.

Conventionally, when a test substance is released from the test substance captured by the antibody (that is, the complex of the antibody and the test substance), an acidic solution is used. This is because an acidic solution generally has an excellent action of dissociating a binding between a test substance and an antibody. For example, Japanese Laid-Open Patent Publication No. 2018-194374 describes that an Aβ peptide is released from the complex by an acidic aqueous solution with a pH of 1 to 4, which may contain an organic solvent. However, as shown in the examples described later, the present inventors found that an acidic solution containing a released Aβ peptide is not suitable for mass spectrometry in combination with liquid chromatography. Specifically, when the acidic solution containing the released Aβ peptide was used as it was for liquid chromatography, a phenomenon in which a part of the charged Aβ peptides remained in a flow path and column of a liquid chromatography apparatus and the remaining Aβ peptide was carried over to measurement of next sample (called carryover) occurred. When carryover occurs, accurate measurement of Aβ peptide cannot be performed. In order to reduce carryover, it is conceivable to release the Aβ peptide in an acidic solution and then exchange the solvent with a basic solution. However, even if the carryover can be reduced by this method, it may be difficult to measure with high sensitivity because the Aβ peptide is lost due to solvent exchange. On the other hand, in the measurement method of the present embodiment using a basic solution containing an organic solvent, the amount of Aβ peptide carried over is significantly reduced. Therefore, even if the basic solution containing the released Aβ peptide is used as it is for liquid chromatography, the Aβ peptide can be accurately measured and no solvent exchange is required. As described above, since a blood sample has a lower content of Aβ peptide than CSF, the measurement method of the present embodiment is suitable for quantitative measurement of Aβ peptide in the blood sample.

In the measurement method of the present embodiment, first, an antibody that specifically binds to an Aβ peptide is mixed with a blood sample containing an Aβ peptide to form a complex of the Aβ peptide and the antibody. A complex of an Aβ peptide and an antibody can be formed by mixing a blood sample containing an Aβ peptide with an antibody that specifically binds to the Aβ peptide.

As used herein, the term "blood sample containing an Aβ peptide" also includes blood samples suspected of containing an Aβ peptide. Examples of the blood samples include blood (whole blood), plasma, serum, and the like. Of these, plasma and serum are preferred. The blood sample may be diluted with an appropriate aqueous medium as necessary. The aqueous medium is not particularly limited as long as it does not interfere with the measurement described later. Examples of the aqueous medium include water, physiological saline, a buffer solution, and the like. The buffer solution is a buffer solution having a buffering effect at a pH near neutrality (for example, a pH of 6 or more and 8 or less). Examples of the buffer solution include Good buffers such as HEPES, MES, and PIPES, tris buffered saline (TBS), phosphate buffered saline (PBS), and the like.

An origin of the blood sample is not particularly limited. For example, the blood sample may be blood collected from a subject and plasma or serum prepared from the blood. Commercially available pool plasma, healthy person plasma or the like may be used. A labeled Aβ peptide as an internal standard substance may be added to the blood sample as necessary. The subject is not particularly limited. Examples of the subject include a healthy person, a person having abnormality in cognitive function, and a person suspected of having the abnormality. Examples of cognitive dysfunction include mild cognitive impairment (MCI), Alzheimer's disease, and the like.

Aβ peptide is a polypeptide produced by treating amyloid β precursor protein (APP) with β-secretase and γ-secretase. Unless otherwise specified, Aβ peptides include polypeptides of any length, but are usually polypeptides consisting of 39 to 43 amino acids. As the Aβ peptide, Aβ40 (DAEFRHDSGYEVHHQKLVFFAEDVGSNKGAIIGL-MVGGVV: SEQ ID NO: 1) consisting of 40 amino acid residues and Aβ42 (DAEFRHDSGYEVHHQKLVFFAEDVGSNKGAIIGL-MVGGVVIA: SEQ ID NO: 2) consisting of 42 amino acid residues are preferable.

The Aβ peptide may be in the form of a monomer or a multimer. A multimer, also called a polymer, is formed by physically or chemically polymerizing or aggregating a plurality of monomeric Aβ peptides. The multimer may contain a plurality of monomeric Aβ peptides, and may contain other molecules. In the multimer, the monomeric Aβ peptides do not need to be tightly bound to each other by covalent bonds or the like. Multimers also include aggregates in which a plurality of monomeric Aβ peptides are aggregated by looser binding. Examples of the multimer of Aβ peptide include Aβ oligomers and the like.

As used herein, the term "antibody" includes full-length antibodies and fragments thereof. Examples of the antibody fragments include Fab, Fab', F(ab')2, Fd, Fd', Fv, light chain, heavy chain variable region (VHH) of heavy chain antibody, reduced IgG (rIgG), one chain antibodies (scFv), and the like. The antibody that specifically binds to an Aβ peptide may be either a monoclonal antibody or a polyclonal antibody, but is preferably a monoclonal antibody.

The monoclonal antibody itself that can specifically bind to the Aβ peptide is known. Examples thereof include an antibody of clone 82E1 (called 82E1 antibody) that recognizes 1st to 16th regions counting from an N-terminal amino acid residue of the Aβ peptide as an epitope, an antibody of clone 6E10 (called 6E10 antibody) that recognizes 3rd to 8th regions as an epitope, an antibody of clone WO-2 (called WO-2 antibody) that recognizes 4th to 10th regions as an epitope, an antibody of clone 2H4 (called 2H4 antibody) that recognizes 1st to 8th regions as an epitope, an antibody of clone H31L21 (called H31L21 antibody) that recognizes 36th to 42nd regions as an epitope, an antibody of clone G2-11 (called G2-11 antibody) that recognizes 33rd to 42nd regions as an epitope, an antibody of clone 16C11 (called 16C11 antibody) that recognizes 33rd to 42nd regions as an epitope, an antibody of clone 21F12 (called 21F12 antibody) that recognizes 34th to 42nd regions as an epitope, an antibody of clone 1A10 (called 1A10 antibody) that recognizes 35th to 40th regions as an epitope, and the like. These monoclonal antibodies are commercially available.

In the present embodiment, it is preferable to use an antibody that binds to one or both of Aβ40 and Aβ42 as an antibody that specifically binds to the Aβ peptide. Examples of the antibody that specifically binds to Aβ40 include an antibody of clone 1A10. Examples of the antibody that specifically binds to Aβ42 include antibodies of clones H31L21, G2-11, 16C11 and 21F12. Examples of the antibody that binds to both Aβ40 and Aβ42 include antibodies of clones 82E1, 6E10, WO-2 and 2H4. By using these antibodies, Aβ40 and/or Aβ42 can be selectively captured among the Aβ peptides in the blood sample. In this case, at least one of Aβ40 or Aβ42 can be released in releasing of the measurement method of the present embodiment, and a measured value of the at least one of Aβ40 or Aβ42 can be acquired in measuring.

In a preferred embodiment, an antibody that binds to both Aβ40 and Aβ42 is used. In this case, Aβ40 and Aβ42 can be released in the releasing of the measurement method of the present embodiment, and a measured value of Aβ40 and a measured value of Aβ42 can be acquired in the measuring.

In the measurement method of the present embodiment, it is preferable to form a complex of the Aβ peptide and the antibody on the solid phase in order to selectively acquire the Aβ peptide captured by the antibody. The complex can be formed on the solid phase by contacting a solution containing the complex with a solid phase on which the antibody can be immobilized. Alternatively, an antibody that specifically binds to the Aβ peptide may be previously immobilized on the solid phase and used. By using an antibody immobilized on the solid phase, the complex can be formed on the solid phase. Specifically, the complex is formed on the solid phase by mixing the solid phase on which the antibody that specifically binds to the Aβ peptide is immobilized and the blood sample. Then, the complex can be selectively acquired by separating an unreacted free component and the solid phase and recovering the solid phase.

The solid phase may be any insoluble carrier capable of immobilizing an antibody. The mode of immobilization of the antibody on the solid phase is not particularly limited. For example, the antibody and the solid phase may be bound directly, or the antibody and the solid phase may be indirectly bound via another substance. Examples of the direct binding include physical adsorption and the like. Examples of the indirect binding include immobilizing a molecule that specifically binds to an antibody on a solid phase, and immobilizing the antibody on the solid phase through binding between the molecule and the antibody. Examples of the molecule that specifically binds to the antibody include protein A or G, an antibody (a secondary antibody) that specifically recognizes an antibody, and the like. A combination of substances interposed between the antibody and the solid phase can be used to immobilize the antibody on the solid phase. Examples of the combination of substances include combinations of any of biotin and its analogs and any of biotin-binding sites, a hapten and an anti-hapten antibody and the like. The biotin and its analogs include biotin and biotin analogs such as desthiobiotin and oxybiotin. The biotin-binding sites include avidin and avidin analogs such as streptavidin and tamavidin (registered trademark). Examples of the combination of a hapten and an anti-hapten antibody include a combination of a compound having a 2,4-dinitrophenyl (DNP) group and an anti-DNP antibody. For example, by using an antibody previously modified with biotin or its analog (or a compound having a DNP group) and a solid phase to which a biotin-binding site (or anti-DNP antibody) is previously bound, the antibody can be immobilized on the solid phase through binding between the biotin or its analog and the biotin-binding site (or binding between the DNP group and the anti-DNP antibody).

The material of the solid phase is not particularly limited. For example, the material can be selected from organic polymer compounds, inorganic compounds, biopolymers, and the like. Examples of the organic polymer compounds include latex, polystyrene, polypropylene, styrene-methacrylic acid copolymer, styrene-glycidyl (meth)acrylate copolymer, styrene-styrene sulfonate copolymer, methacrylic acid polymer, acrylic acid polymer, acrylonitrile butadiene styrene copolymer, vinyl chloride-acrylate copolymer, polyvinyl acetate acrylate, and the like. Examples of the inorganic compounds include magnetic bodies (iron oxide, chromium oxide, cobalt, ferrite, etc.), silica, alumina, glass, and the like. Examples of the biopolymer include insoluble agarose, insoluble dextran, gelatin, cellulose, and the like. Two or more of these may be used in combination. The shape of the solid phase is not particularly limited. Examples of the shape of the solid phase include a particle, a microplate, a microtube, a test tube, and the like. Among them, particles are preferable, and magnetic particles are particularly preferable. When a particle is used as the solid phase, a complex forming in the measurement method of the present embodiment corresponds to a general immunoprecipitation method.

Subsequently, in the measurement method of the present embodiment, the Aβ peptide is released from the complex with a basic solution containing an organic solvent (hereinafter, also referred to as "free reagent"). The free reagent is considered to have an action of dissociating the binding between the antibody and the Aβ peptide. In a preferred embodiment, the solution containing the complex formed on the solid phase is mixed with the free reagent. As a result, the Aβ peptide is released from the complex, and the released Aβ peptide and the solid phase on which the antibody is immobilized are present in the mixed solution. For example, when the solid phase is a magnetic particle, a solution containing the Aβ peptide can be recovered by separating the solid phase on which the antibody is immobilized and the solution containing the Aβ peptide by centrifugation or magnetic separation.

Conditions for contact between the complex and the free reagent are not particularly limited. For example, the free reagent at a temperature of 4° C. or more and 42° C. or less is contacted with the complex and allowed to stand or agitated for 1 minute or more and 10 minutes or less. An amount of the free reagent used is not particularly limited. For example, the amount can be appropriately determined, for example, from the range of 10 μL or more and 50 μL or less per sample.

The free reagent can be obtained by mixing a basic solution with an organic solvent, or by mixing water with a basic substance and an organic solvent. The basic solution can be obtained by mixing water and a basic substance. A commercially available basic solution such as aqueous ammonia may be used. Examples of the basic substance include a substance that donates an ammonium ion and the like. Examples of the substance that donates an ammonium ion include ammonia, ammonium carbonate, ammonium bicarbonate, and the like. The basic substance in the free reagent may be one type or two or more types.

Examples of the organic solvent include acetonitrile, acetone, 1-propanol, 2-propanol, hexane, ethanol, dimethyl sulfoxide, methanol, and the like. The organic solvent in the free reagent may be one type or two or more types. In the present embodiment, the free reagent preferably contains at least acetonitrile as the organic solvent, and more preferably contains only acetonitrile as the organic solvent.

The concentration of the organic solvent in an elution reagent is not particularly limited, and is preferably 20% or more, 30% or more, or 40% or more. The concentration of the organic solvent is preferably 65% or less, 60% or less, or 55% or less. The concentration "%" of the organic solvent as used herein is all volume/volume % (v/v %).

A pH of the free reagent is not particularly limited as long as it is a pH recognized as basic by those skilled in the art. The pH of the free reagent is preferably 10.85 or more, 10.9 or more, 10.95 or more, 11.0 or more, 11.05 or more, 11.1 or more, 11.15 or more, 11.2 or more, 11.25 or more, 11.3 or more, 11.35 or more, or 11.4 or more. Most preferably, the free reagent has a pH of 11.4 or more. As a result, the Aβ peptide can be released from the complex particularly efficiently. The pH of the free reagent is preferably 14.0 or less, 13.5 or less, 13.0 or less, 12.5 or less, 12.4 or less, 12.35 or less, 12.3 or less, 12.25 or less, 12.2 or less, 12.15 or less, 12.1 or less, 12.05 or less, or 12.0 or less.

The pH of the free reagent can be adjusted by an amount (or concentration) of basic substance added. When ammonia or a salt thereof is used as the basic substance, the molar concentration of ammonium ions in the free reagent is preferably 5.29 mM or more, 10.57 mM or more, 26.43 mM or more, 52.85 mM or more, 105.71 mM or more, or 132.14 mM or more. The molar concentration is preferably 1586 mM or less, 1533 mM or less, or 1480 mM or less. For example, when the basic substance is ammonia, the concentration of ammonia in the free reagent is preferably 0.01% or more, 0.02% or more, 0.05% or more, 0.1% or more, 0.2% or more, or 0.25% or more. The concentration is preferably 3% or less, 2.9% or less, or 2.8% or less. The concentration "%" of ammonia as used herein is all weight/weight % (w/w %).

The measurement method of the present embodiment may include washing step of removing an unreacted free component that has not formed a complex between the complex forming and the releasing. This washing includes B/F (Bound/Free) separation. The unreacted free component is a component that does not constitute a complex, and examples thereof include antibodies that have not bound to an Aβ peptide. The washing method is not particularly limited, and in a case where the complex is formed on a solid phase, when the solid phase is a particle, the complex and the unreacted free component can be separated by recovering the particle by centrifugation or magnetic separation, and removing supernatant. When the solid phase is a container such as a microplate or a microtube, the complex and the unreacted free component can be separated by removing a liquid containing the unreacted free component. After removing the unreacted free component, the solid phase capturing the complex may be washed with a suitable aqueous medium such as PBS.

Then, in the measurement method of the present embodiment, the released Aβ peptide is measured by mass spectrometry. The mass spectrometry is not particularly limited as long as the released Aβ peptide can be measured, and a known ionization capable of measuring the Aβ peptide can be used. Examples of the ionization include electrospray ionization (ESI), atmospheric chemical ionization (APCI), matrix-assisted laser desorption ionization (MALDI), and the like. Among them, the ESI method is particularly preferred.

The mass spectrometer used in the mass spectrometry is not particularly limited, and the mass spectrometer can be appropriately selected from known mass spectrometers. Examples thereof include a quadrupole (Q) mass spectrometer, ion trap (IT) mass spectrometer, a flight time (TOF) mass spectrometer, a Fourier transform ion cyclotron resonance (FTICR) mass spectrometer, an IT-TOF type mass spectrometer, a Q-TOF type mass spectrometer, a triple quadrupole (QqQ) type mass spectrometer, and the like. Among them, it is preferable to measure using a mass spectrometer capable of MS/MS measurement, and more preferably to measure using a triple quadrupole mass spectrometer.

In mass spectrometry, liquid chromatography-mass spectrometry (LC-MS), which is a combination of a mass spectrometer and a liquid chromatography apparatus, is preferably used, and LC-MS/MS which is a combination of liquid chromatography with a mass spectrometer capable of MS/MS measurement is preferably used.

The liquid chromatography apparatus is not particularly limited as long as it can be connected to a mass spectrometer, and a commercially available high performance liquid chromatography (HPLC) apparatus can be used. The column connected to the liquid chromatography apparatus is not particularly limited, and a commercially available column for HPLC can be used. In the present embodiment, the Aβ peptide released in the free reagent can be subjected to a liquid chromatography apparatus. Therefore, pre-measurement process such as solvent exchange is not required.

The column is not particularly limited, but for example, a reversed-phase column can be used. Examples of a filler of the reversed-phase column include a silica-based filler, a polymer-based filler, and the like. Among them, a silica-based filler is preferred. As the reversed-phase column having a silica-based filler, a basic-resistant ODS column is more preferred.

As the solvent (mobile phase) used for liquid chromatography, a solution having the same composition as the free reagent or a basic solution used for the free reagent can be used. The concentration of organic solvent in the mobile phase is not particularly limited, and the concentration can be appropriately set according to measurement conditions. Liquid chromatography may be performed using an isocratic method using a mobile phase with a single concentration. Alternatively, liquid chromatography may be performed using a stepwise method or a gradient method in which a plurality of mobile phases with different compositions are used in combination.

Flow velocity of the mobile phase in the measurement can be appropriately set according to properties such as materials of the apparatus and the column and pressure resistance. The flow velocity of the mobile phase is preferably set to a flow velocity at which mass spectrometry is appropriately performed. The column temperature, the amount of a sample introduced into a measuring apparatus and the like can be appropriately set according to the measuring apparatus and the column.

In the measurement method of the present embodiment, measurement may be performed by a liquid chromatography apparatus to acquire information about the sample. Examples of the detector that performs measurement include a UV detector, a fluorescence detector, a differential refractive index detector, an electrical conductivity detector, an electrochemical detector, and the like.

The measurement of Aβ peptide by mass spectrometry can be appropriately set from a known technique according to the ionization and the mass spectrometer to be used. Among them, when a triple quadrupole mass spectrometer is used, it is preferable that the Aβ peptide is measured by multiple reaction monitoring (MRM) measurement in which the measurement mode is set to positive ion measurement mode.

The triple quadrupole mass spectrometer has a first quadrupole (Q1) and a third quadrupole (Q3) in front of and behind a collision cell (Q2). An object to be measured is ionized by an ion source to be precursor ions, and only ions having a specific mass-to-charge ratio (m/z) set in Q1 pass through a filter and are introduced into Q2. The precursor ions with a specific mass-to-charge ratio introduced into Q2 collide with an inert gas and cleave to be product ions. The product ions sent from Q2 to Q3 are filtered again in Q3, only ions with a specific mass pass through the filter and are sent from Q3 to a detector, and a signal is detected. As a result, a specific product ion for a specific precursor ion is detected by the detector. A combination of the specific mass-to-charge ratio set in Q1 and the specific mass-to-charge ratio set in Q3 is called an MRM transition. In MRM measurement, by setting multiple MRM transitions, multiple product ions can be detected at the same time. As a result, a plurality of substances contained in the object to be measured can be measured at the same time. For example, each MRM transition is set for a sample containing Aβ40 and Aβ42, whereby two types of Aβ peptides can be measured at the same time and each measured value can be acquired.

In the MRM measurement, the measurement mode is not particularly limited, but it is preferable to use the mass spectrometer in the positive ion measurement mode. Cone voltage and collision energy in the MRM measurement are also not particularly limited. The cone voltage and collision energy can be set to appropriate conditions by those skilled in the art.

For example, as an MRM transition for Aβ40, precursor ion/product ion can be set to 1083/1953.6. As an MRM transition for Aβ42, precursor ion/product ion can be set to 1129/1078.5. By setting the MRM transitions as described above, the Aβ peptide can be detected with high sensitivity.

In the measurement method of the present embodiment, the blood sample may be mixed with a labeled internal standard substance, and the measured value of the Aβ peptide may be acquired based on the measured value of the internal standard substance. The internal standard substance is not particularly limited as long as it can quantify the Aβ peptide, but the internal standard substance is preferably an Aβ peptide labeled with a stable isotope. Examples of the Aβ peptide labeled with a stable isotope include Aβ40 and Aβ42 labeled with N15 stable isotope. The amount of the internal standard substance added is not particularly limited as long as the concentration can be measured by the measuring apparatus. The amount of the internal standard substance added can be appropriately set according to analytical ability of the measuring apparatus.

In addition to the MRM transition for detecting the Aβ peptide, an MRM transition can be set and measured for the Aβ peptide labeled with a stable isotope as the internal standard substance, and the measured value can be acquired. As the MRM transition for Aβ40 labeled with N15 stable isotope, precursor ion/product ion can be set to 1096/1066.5. As the MRM transition for Aβ42 labeled with N15 stable isotope, precursor ion/product ion can be set to 1142.5/1091.5.

A further embodiment is a reagent composition used in the measurement method of the present embodiment. This reagent composition is a basic solution containing an organic solvent. The basic solution containing an organic solvent is as described above. By using the reagent composition, the Aβ peptide can be released with high efficiency from a complex of the Aβ peptide and the antibody that specifically binds to the Aβ peptide.

A pH of the reagent composition is not particularly limited as long as it is a pH recognized as basic by those skilled in the art. The pH of the reagent composition is preferably 10.85 or more, 10.9 or more, 10.95 or more, 11.0 or more, 11.05 or more, 11.1 or more, 11.15 or more, 11.2 or more, 11.25 or more, 11.3 or more, 11.35 or more, or 11.4 or more. Most preferably, the reagent composition has a pH of 11.4 or more. As a result, the Aβ peptide can be released from the complex particularly efficiently. The pH of the reagent composition is preferably 14.0 or less, 13.5 or less, 13.0 or less, 12.5 or less, 12.4 or less, 12.35 or less, 12.3 or less, 12.25 or less, 12.2 or less, 12.15 or less, 12.1 or less, 12.05 or less, or 12.0 or less.

The reagent composition may contain additives such as stabilizers to an extent that it does not affect the release of Aβ peptide from the complex and the measurement of Aβ peptide by mass spectrometry. Examples of the additive include bovine serum albumin (BSA), human albumin, egg white albumin, monosaccharides such as glucose, disaccharides such as maltose, sugar alcohols such as mannitol and sorbitol, amino acids such as glycine, and the like. The additive may be one type or two or more types. The additive is preferably contained in the range of 0 parts by weight or more and 20 parts by weight or less based on 100 parts by weight of the basic solution containing an organic solvent. The reagent composition may be contained in a suitable container that does not affect composition of the reagent composition. FIG. 1 is a diagram showing an example of a container 151 containing the reagent composition.

Hereinafter, the present disclosure will be described more specifically with reference to Examples.

EXAMPLES

Example 1: Measurement of Plasma Aβ Peptide Using Combination of Immunoprecipitation Using Basic Solution Containing an Organic Solvent and Mass Spectrometry An Aβ peptide was released from a complex of an Aβ peptide and an antibody that specifically binds to the Aβ peptide using a basic solution containing an organic solvent, and the Aβ peptide was measured using mass spectrometry.

(1) Capture and Release of Aβ Peptide Using Immunoprecipitation (1.1) Blood Sample As blood samples containing an Aβ peptide, 5 types of commercially available plasma samples (ProMedeX) from different lots were used.

(1.2) Antibody that Specifically Binds to Aβ Peptide

As an antibody that specifically binds to the Aβ peptide, 6E10 antibody (BioLegend, Inc.) which is a commercially available mouse monoclonal anti-Aβ antibody was used. The 6E10 antibody was immobilized on a magnetic particle (M-270 Epoxy-activated Dynabeads: Thermo Fisher Scientific Inc.) by a conventional method.

(1.3) Aβ Peptide

An Aβ40 peptide and an Aβ42 peptide were purchased from AnaSpec, Inc. for preparation of a calibration curve. As internal standard substances, 15N-Aβ40 and 15N-Aβ42 (rPeptide) which were an Aβ40 peptide and an Aβ42 peptide each labeled with a stable isotope $^{15}$N were used. The Aβ40 peptide was suspended in PBS solutions containing 3% BSA, so as to have final concentrations of 10.8 pg/ml, 21.7 pg/ml, 43.3 pg/ml, 86.6 pg/ml, 173.2 pg/ml, 346.4 pg/ml and 692.8 pg/ml, respectively. The Aβ42 peptide was suspended in PBS solutions containing 3% BSA, so as to have final concentrations of 2.8 pg/ml, 5.6 pg/ml, 11.3 pg/ml, 22.6 pg/ml, 45.2 pg/ml, 90.3 pg/ml and 180.6 pg/mL, respectively. 15N-Aβ40 and 15N-Aβ42 were suspended in the same solution in PBS solutions containing 3% BSA so as to be 500 pg/ml, respectively.

(1.4) Preparation of Basic Solution Containing Organic Solvent

As a basic solution (free reagent) containing an organic solvent, 1.2 ml of 28% concentrated ammonia water (Nacalai Tesque, Inc.) and 6.0 ml of acetonitrile (Kanto Chemical Co., Inc.) were added and mixed to 12.8 ml of pure water to prepare a 1.68% ammonia/30% acetonitrile solution.

(1.5) Immunoprecipitation

A 250 μl of plasma sample or each of the Aβ40 peptide solutions or Aβ42 peptide solution prepared in (1.3) above was added to a 1.5 ml sample tube (Eppendorf AG). To each sample tube containing the above solution was added 250 μl of the solution containing 15N-Aβ40 and 15N-Aβ42 prepared in (1.3) above, and the sample tube was allowed to stand at room temperature for 30 minutes. After standing the sample tube, 40 μl of the suspension of magnetic particles (4 μg antibody/0.4 mg magnetic particles) immobilized with 6E10 antibody prepared in (1.2) above was added to each sample solution, and the mixture was inverted and mixed for 1 hour using a rotator at room temperature to form a complex of the Aβ peptide and the antibody. These solutions were focused using a magnetic stand to remove supernatant.

(1.6) Washing

After removing the supernatant, 1 mL of a PBS solution containing 3% BSA was added to the magnetic particles remaining in the sample tube, mixed, and then magnetized again to remove supernatant. This operation was performed twice with 1 mL of the PBS solution containing 3% BSA, twice with 1 mL of a 50 mM ammonium acetate solution and once with 1 mL of ultrapure water successively to wash the magnetic particles.

(1.7) Release of Aβ Peptide from Complex

After washing the magnetic particles in (1.6) above, 25 μL of the free reagent prepared in (1.4) above was added to the remaining magnetic particles after removing the washing liquid, mixed, and the mixture was allowed to stand for 1 minute. The magnetic particles were magnetically collected again, and supernatant was recovered as an eluate.

(2) Mass Spectrometry

The eluate prepared in (1.7) above was subjected to LC-MS/MS for MRM measurement, and the Aβ peptide was measured. ACQUITY (registered trademark) UPLC (registered trademark) H-class biosystem (Waters Corporation: hereinafter also referred to as UPLC) was used for a liquid chromatography section of LC-MS/MS. As the column, an ACQUITY (registered trademark) UPLC (registered trademark) peptide BEH $C_{18}$ column (Waters Corporation) which is a reversed-phase column was used. As the mass spectrometer, Xevo (registered trademark) TQ-XS triple quadrupole mass spectrometer (Waters Corporation: hereinafter also referred to as TQ-XS mass spectrometer) was used.

Each eluate was placed on a UPLC autosampler, and 10 μl of the eluate was introduced into the UPLC and fractionated by gradient. Conditions for the gradient were as follows.

TABLE 1

| | |
|---|---|
| Analysis device | Xevo TQ-XS triple quadrupole mass spectrometer |
| Column | ACQUITY UPLC Peptide BEH $C_{18}$ column (300 Å, 1.7 μm, 2.1 mm × 150 mm) |
| Introduction amount | 10 μl |
| Flow rate | 200 μl/min |
| Temperature | 50° C. |
| Mobile phase A | 0.1% Ammonia solution |
| Mobile phase B | 0.01% Ammonia, 90% Acetonitrile solution |

TABLE 1-continued

| | | |
|---|---|---|
| Gradient conditions | 0 to 1.0 minutes | 90% A, 10% B |
| | 1.0 to 5.5 minutes | 90-45% A, 10-55% B |
| | 5.5 to 6.7 minutes | 45% A, 55% B |
| | 6.7 to 7.0 minutes | 45-90% A, 55-10% B |
| | 7.0 to 8.5 minutes | 90% A, 10% B |

An eluate that was subjected to the gradient and eluted from the column was directly subjected to the TQ-XS mass spectrometer connected to the UPLC. The TQ-XS mass spectrometer used electrospray ionization and measured in positive ion mode. Conditions for MRM measurement were set as shown in Table 2 below.

TABLE 2

| | Precursor ion (m/z) · 4+ | Product ion (m/z) · 4+ | Cone voltage (V) | Collision energy (eV) |
|---|---|---|---|---|
| A β 40 | 1083.4 | 1054.0 | 32 | 22 |
| A β 42 | 1129.5 | 1078.8 | 28 | 25 |
| 15N-A β 40 | 1096 | 1066.5 | 32 | 22 |
| 15N-A β 42 | 1142.6 | 1091.5 | 28 | 25 |

(3) Measurement Results

Figure 2:
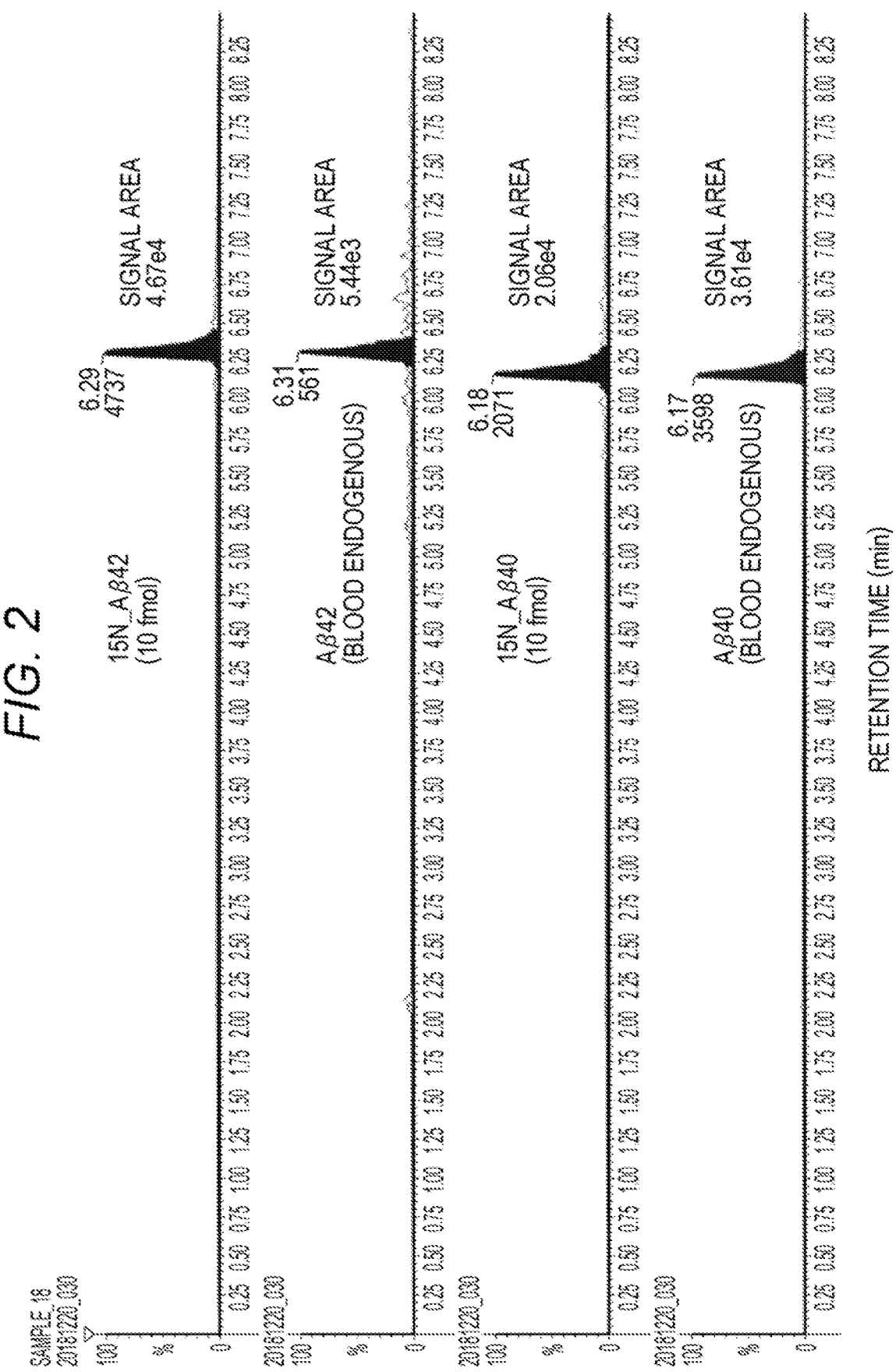
FIG. 2 is a diagram showing results of measurement of Aβ peptide using LC-MS/MS.
Figure 3A:
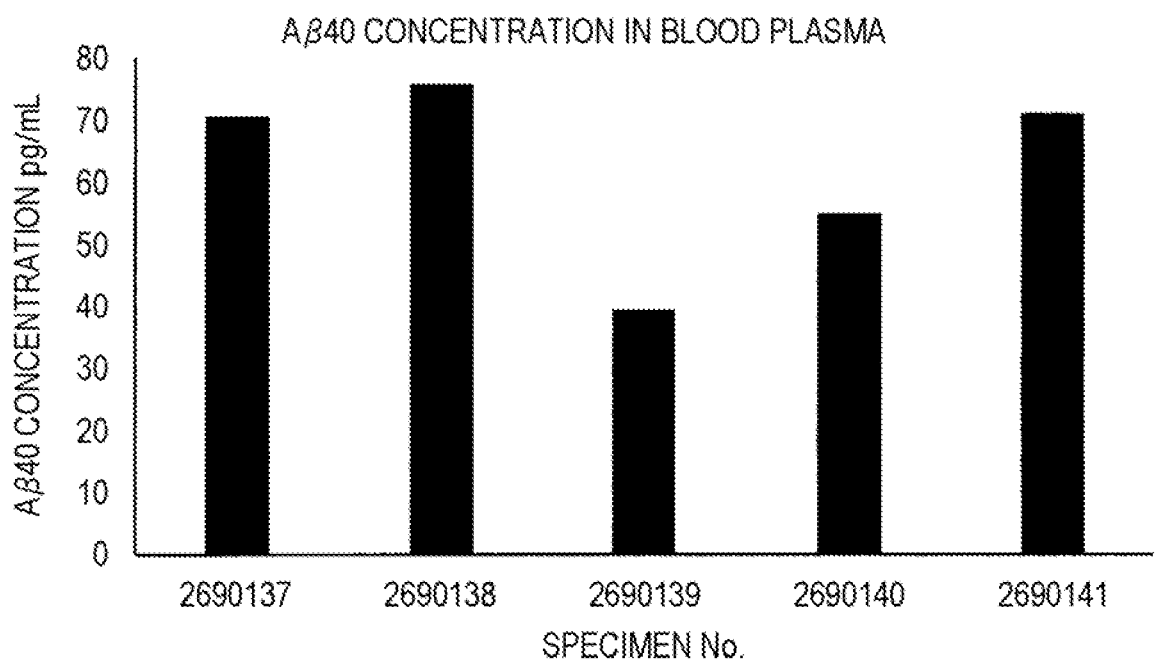
FIG. 3A is a diagram showing concentrations of Aβ40 peptide in plasma of each specimen.
Figure 3B:
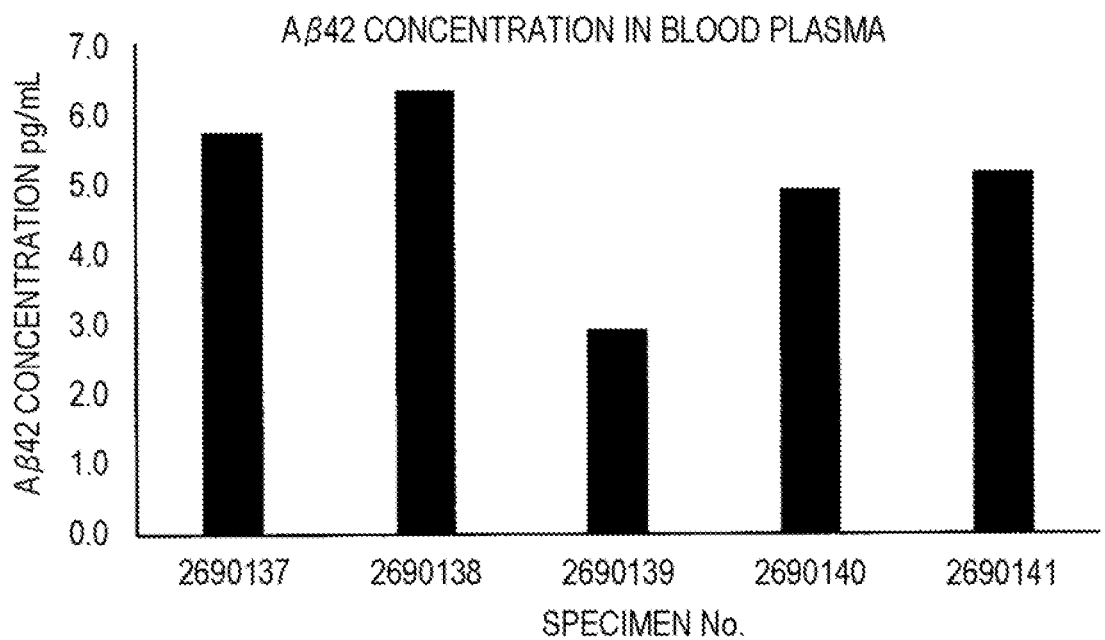
FIG. 3B is a diagram showing concentrations of Aβ42 peptide in plasma of each specimen.

Measurement results using LC-MS/MS are shown in FIGS. 2, 3A and 3B. FIG. 2 shows results of MRM measurement for Aβ40 peptide, Aβ42 peptide, 15N-Aβ40 and 15N-Aβ42, and FIGS. 3A and 3B show concentrations of Aβ40 peptide and Aβ42 peptide in the measured plasma specimens. From these results, it was shown that the Aβ peptide can be released from the complex using a basic solution containing an organic solvent and the Aβ peptide can be measured by mass spectrometry.

Figure 4A:
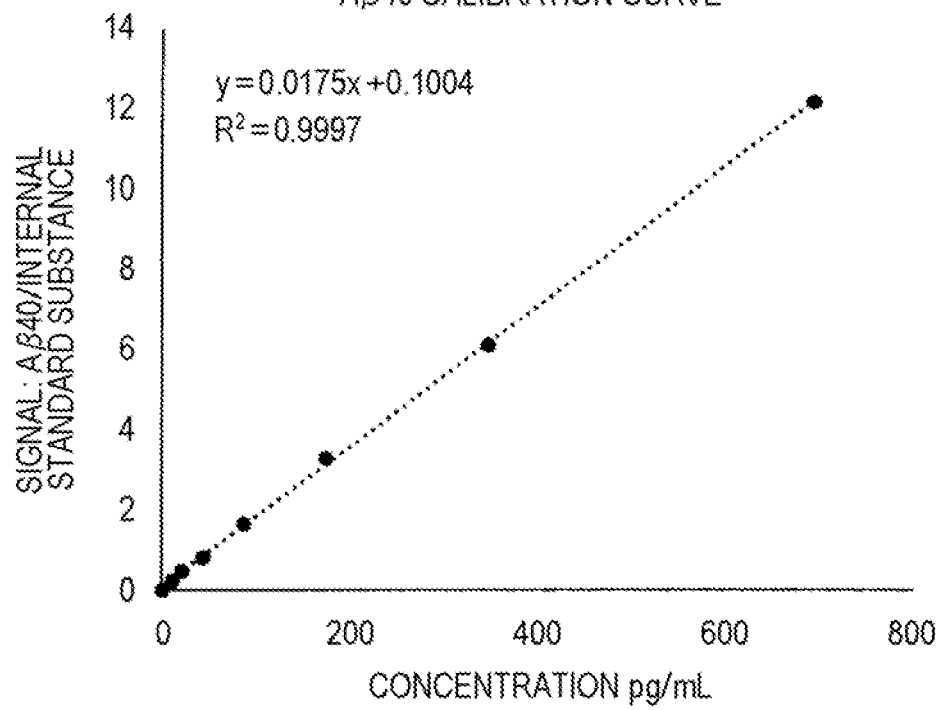
FIG. 4A is a diagram showing a calibration curve prepared based on measured values detected using an Aβ40 peptide with a known concentration.
Figure 4B:
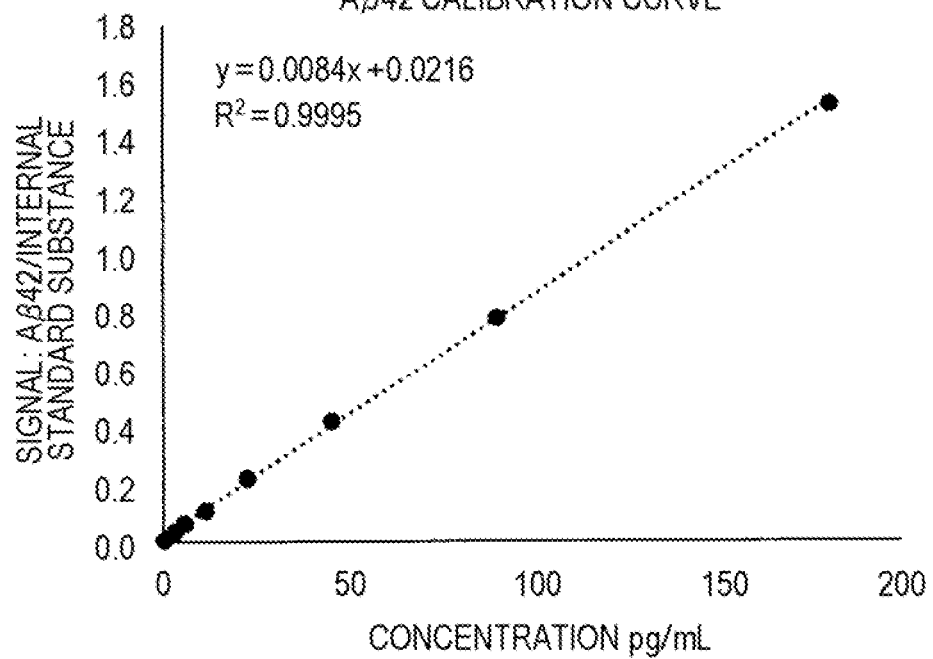
FIG. 4B is a diagram showing a calibration curve prepared based on measured values detected using an Aβ42 peptide with a known concentration.

FIGS. 4A and 4B show results of preparing a calibration curve based on the measured values detected using the Aβ peptide with a known concentration prepared in (1.3) above. As shown in FIGS. 4A and 4B, it was possible to prepare a calibration curve in which $R^2$ was 0.999 or more in both the Aβ40 peptide and the Aβ42 peptide. Low concentrations of Aβ peptide of 100 pg/ml or less were also detectable. From this, it was shown that the above measurement method which is a combination of a basic solution containing an organic solvent and mass spectrometry can measure Aβ peptide with high sensitivity and has excellent quantitative properties.

Example 2: Comparison of Elution Efficiency

The composition of the free reagent was changed, and an elution efficiency of Aβ peptide from the complex due to difference in the composition of the free reagent was calculated based on the following calculation formula and compared.

[Elution efficiency (%)]=[Aβ peptide concentration of sample C]/([Aβ peptide concentration of sample A]−[Aβ peptide concentration of sample B])×100

(1) Comparison of Basic Substances in Free Reagents
(1.1) Preparation of Free Reagent DDM (n-dodecyl-β-D-maltoside, Sigma-Aldrich Co. LLC.), acetonitrile and/or 28% concentrated ammonia water were appropriately selected and mixed with pure water so as to have the compositions shown in Table 3 below to prepare various free reagents. Here, a solution containing no basic substance or organic solvent was also referred to as a free reagent for convenience. After preparation, pH of the solution containing the basic substance was measured using a pH meter (HORIBA, Ltd.).

TABLE 3

| | Free reagent composition | pH |
|---|---|---|
| Comparative reagent 1 | DDM, 70% Acetonitrile | |
| Comparative reagent 2 | DDM, 0.056% Ammonia | 11.013 |
| Comparative reagent 3 | DDM, 0.56% Ammonia | 11.582 |
| Reagent 1 | 50% Acetonitrile, 0.028% Ammonia | 10.854 |
| Reagent 2 | 50% Acetonitrile, 0.07% Ammonia | 11.059 |
| Reagent 3 | 50% Acetonitrile, 0.14% Ammonia | 11.219 |
| Reagent 4 | 50% Acetonitrile, 0.28% Ammonia | 11.448 |
| Reagent 5 | 50% Acetonitrile, 0.56% Ammonia | 11.613 |
| Reagent 6 | 50% Acetonitrile, 1.12% Ammonia | 11.801 |
| Reagent 7 | 50% Acetonitrile, 1.68% Ammonia | 11.973 |
| Reagent 8 | 50% Acetonitrile, 2.24% Ammonia | 11.974 |
| Reagent 9 | 50% Acetonitrile, 2.80% Ammonia | 12.038 |

(1.2) Sample Preparation

Sample A was prepared by suspending the Aβ40 peptide used in (1.3) of Example 1 in a PBS solution containing 3% BSA so as to be 1000 pg/ml. The Aβ peptide concentration of sample A corresponds to an initial concentration of Aβ40 peptide.

(1.3) Immunoprecipitation

The sample A prepared in (1.2) above was immunoprecipitated in the same manner as in (1.5) of Example 1 to recover magnetic particles. At this time, supernatant after magnetization was collected and stored as sample B. An Aβ peptide concentration of sample B corresponds to a concentration of Aβ peptide that could not be captured by an antibody that specifically binds to the Aβ peptide.

(1.4) Washing/Elution

The magnetic particles recovered in (1.3) above were washed in the same manner as in (1.6) of Example 1, and a washing liquid was removed. To the washed magnetic particles was added 15 µl of each of the free reagents prepared in (1.1) above, and the mixture was allowed to stand for 1 minute to release the Aβ peptide. After standing the mixture, the magnetic particles were magnetically collected and supernatant was collected. A pH neutralizing solution (pH 7.4) containing 300 mM Tris and 300 mM NaCl was mixed with the collected supernatant to obtain sample C. The Aβ peptide concentration of the sample C corresponds to the concentration of Aβ peptide released after capture by immunoprecipitation.

(2) Measurement by Immunoassay

For the above samples A, B and C, the Aβ peptide concentration in each sample was measured by an immunoassay using a fully automated immunoassay system HISCL (registered trademark)-5000 (Sysmex Corporation). An R1 reagent (capture antibody reagent) was prepared by labeling 82E1 antibody with biotin by a conventional method and dissolving it in a buffer at pH 7.5 containing 1% BSA, 0.1 M Tris-HCl, 0.15 M NaCl and 0.1% NaN₃. As an R2 reagent (solid phase), a HISCL (registered trademark) R2 reagent (Sysmex Corporation) containing streptavidin-bound magnetic particles was used. An R3 reagent (detection antibody reagent) was prepared by labeling 1A10 antibody with alkaline phosphatase (ALP) by a conventional method and dissolving it in a buffer at pH 7.5 containing 1% BSA, 0.1 M Tris-HCl, 0.15 M NaCl and 0.1% NaN₃. As an R4 reagent (measurement buffer solution), a HISCL (registered trademark) R4 reagent (Sysmex Corporation) was used. As an R5 reagent (ALP substrate solution), a HISCL (registered trademark) R5 reagent (Sysmex Corporation) was used.

Measurement procedure according to HISCL (registered trademark)-5000 was as follows. The sample A, B or C (30 µL) and the R1 reagent (110 µL) were mixed and reacted at 42° C. for 4 minutes. After the reaction, the R2 reagent (30 µL) was added, and the mixture was reacted at 42° C. for 3 minutes. The magnetic particles in the obtained mixed solution were magnetically collected, supernatant was removed, and a HISCL (registered trademark) washing liquid (300 µL) was added to wash the magnetic particles. Supernatant was removed, and the R3 reagent (100 µL) was added to the magnetic particles and mixed, and the mixture was reacted at 42° C. for 5 minutes. The magnetic particles in the obtained mixed solution were magnetically collected, supernatant was removed, and a HISCL (registered trademark) washing liquid (300 µL) was again added to wash the magnetic particles. Supernatant was removed, and the R4 reagent (50 µL) and the R5 reagent (100 µL) were added to the magnetic particles, and the chemiluminescence intensity was measured. As calibrators (antigens for preparing calibration curve), using each of solutions prepared by suspending the Aβ40 peptide in a solution at pH 7.0 containing 0.1% BSA, 0.14 M triethanolamine, 0.15 M NaCl and 0.1% NaN₃ so as to be 0 pg/ml, 8.6 pg/ml, 33.3 pg/ml, 99.2 pg/ml, 319.1 pg/ml and 1188.1 pg/ml, respectively, the same measurement was performed to prepare a calibration curve. The chemiluminescent intensity obtained by the measurement was applied to the calibration curve to determine the concentration of Aβ40 peptide.

(3) Measurement Results

Figure 5:
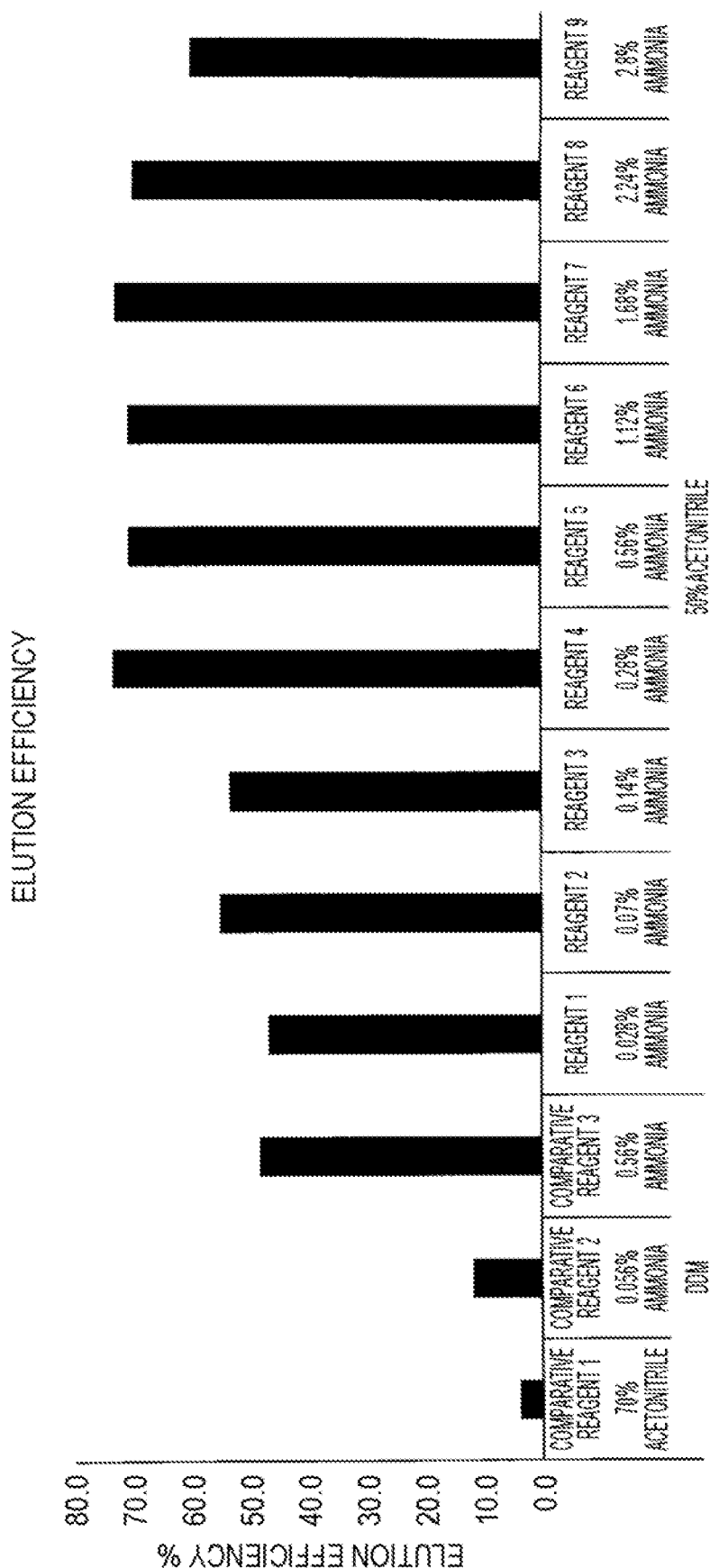
FIG. 5 is a diagram showing difference in elution efficiency of Aβ peptide due to a difference in composition of free reagent.

Measurement results of the elution efficiencies of comparative reagents 1 to 3 and reagents 1 to 9 in Table 3 are shown in FIG. 5. As shown in FIG. 5, it was shown that the elution efficiency is low with the free reagent containing only the organic solvent or the basic solution, and high elution efficiency is obtained when the free reagent containing the organic solvent and the basic substance is used as the free reagent for the Aβ peptide. In particular, it was shown that reagents having a pH of 11.4 or more and 12.0 or less can obtain a high elution efficiency of more than 70%.

(4) Comparison of Free Reagents for Organic Solvents

In (1.1) above, the elution efficiency was measured using the free reagent shown in Table 4 below instead of the free reagent shown in Table 3. In comparative reagent 5 and samples 17 to 23, an Aβ42 peptide was used as a sample instead of the Aβ40 peptide. When the Aβ42 peptide was used, H31L21 antibody was used instead of the 1A10 antibody as a detection antibody, and each of solutions prepared by suspending the Aβ42 peptide in a solution at pH 7.0 containing 0.1% BSA, 0.14 M triethanolamine, 0.15 M NaCl and 0.1% NaN₃ so as to be 0 pg/ml, 0.5 pg/ml, 6.1 pg/ml, 65.2 pg/ml and 804.5 pg/ml, respectively, was used as calibrators. Except for the above, the same operations as in (1) and (2) were carried out, and the elution efficiency of each free reagent was measured.

TABLE 4

| | Free reagent composition | | Free reagent composition |
|---|---|---|---|
| Comparative reagent 4 | 0.56% Ammonia | Comparative reagent 5 | 0.56% Ammonia |
| Reagent 10 | 40% Acetonitrile<br>0.56% Ammonia | Reagent 17 | 40% Acetonitrile<br>0.56% Ammonia |
| Reagent 11 | 40% Acetone<br>0.56% Ammonia | Reagent 18 | 40% Acetone<br>0.56% Ammonia |
| Reagent 12 | 40% 2-Propanol<br>0.56% Ammonia | Reagent 19 | 40% 2-Propanol<br>0.56% Ammonia |
| Reagent 13 | 40% Hexane<br>0.56% Ammonia | Reagent 20 | 40% Hexane<br>0.56% Ammonia |
| Reagent 14 | 40% 1-Propanol<br>0.56% Ammonia | Reagent 21 | 40% 1-Propanol<br>0.56% Ammonia |
| Reagent 15 | 40% Ethanol<br>0.56% Ammonia | Reagent 22 | 40% Ethanol<br>0.56% Ammonia |
| Reagent 16 | 40% DMSO<br>0.56% Ammonia | Reagent 23 | 40% DMSO<br>0.56% Ammonia |

Measurement results for comparative reagent 4 and samples 10 to 16 are shown in FIG. 6A, and measurement results for comparative reagent 5 and samples 17 to 23 are shown in FIG. 6B. From FIGS. 6A and 6B, it was found that samples 10 to 16 and 17 to 23 show better elution efficiency than comparative reagents 4 and 5 containing no organic solvent, and it was shown that the free reagent contains the basic substance and the organic solvent, whereby excellent elution efficiency can be obtained.

Example 3: Carryover Measurement

Conventionally, an acidic solution is used when releasing an Aβ peptide from a complex of the Aβ peptide captured by an antibody and the antibody. Here, carryover of Aβ peptide to a liquid chromatography apparatus was measured under acidic and basic conditions of the free reagent that elutes the complex.
(1) Sample Preparation Here, formic acid (FUJIFILM Wako Pure Chemical Corporation) and acetonitrile were mixed with pure water to prepare an acidic free reagent having a composition of 0.1% formic acid and 50% acetonitrile (here, an acidic solution is also referred to as a free reagent for convenience). A free reagent (1.68% ammonia, 50% acetonitrile) was prepared in the same manner as in (1.4) of Example 1. To these free reagents was added the same Aβ40 peptide as in (1.3) of Example 1 so as to have a final concentration of 100 fmol/ul (Aβ40 peptide-containing solution). A solution containing no Aβ40 peptide (Aβ40 peptide-free solution) was also prepared for each of the acidic free reagent and the basic free reagent.
(2) Introduction of Sample into Liquid Chromatography The four solutions prepared in (1) above were subjected to LC-MS/MS. As an LC-MS/MS apparatus and a column, those described in the mass spectrometry of (2) of Example 1 were used. Each solution was placed on the UPLC autosampler, and 10 μl of each solution was introduced into the UPLC and fractionated. UPLC analysis conditions were as shown in Table 5 below. Conditions for MRM measurement in mass spectrometry are shown in Table 2 of Example 1.

TABLE 5

| | |
|---|---|
| Analysis device | Xevo TQ-XS triple quadrupole mass spectrometer |
| Column | ACQUITY UPLC Peptide BEH $C_{18}$ column<br>(300 Å, 1.7 μm, 2.1 mm × 150 mm) |

TABLE 5-continued

| | |
|---|---|
| Introduction amount | 10 μl |
| Flow rate | 200 μl/min |
| Temperature | 50° C. |
| Mobile phase A | 0.1% Ammonia solution |
| Mobile phase B | 0.01% Ammonia, 90% Acetonitrile solution |
| Elution conditions | 50% A, 50% B |

Figure 7:
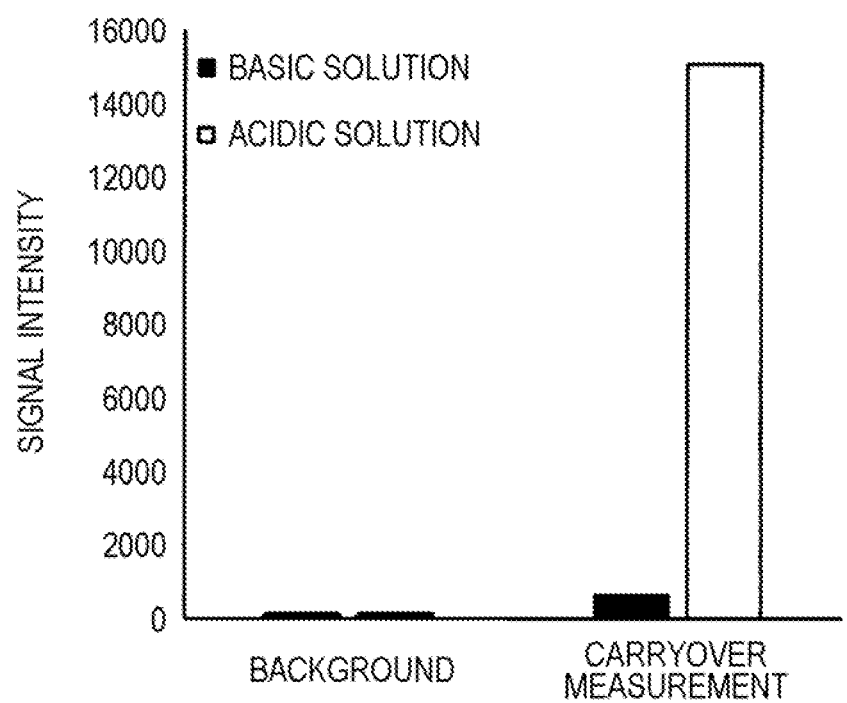
FIG. 7 is a diagram showing a difference in amount of carryover due to a difference in composition of free reagent.

The two types of Aβ40 peptide-containing solutions prepared in (1) above and the corresponding Aβ40-free solutions thereof were subjected to UPLC, in the order of the Aβ40 peptide-free solution (background), Aβ40 peptide-containing solution, and Aβ40 peptide-free solution (carryover measurement). The results of comparing signal intensities obtained at that time are shown in FIG. 7. From FIG. 7, it was found that a large amount of carryover occurred in a case where the acidic free reagent was used as compared with a case where the basic free reagent was used. On the other hand, when the basic free reagent was used as the free reagent for Aβ peptide, carryover could be remarkably suppressed. Therefore, it was shown that it is appropriate to use a basic free reagent for continuous analysis of Aβ peptide using mass spectrometry.

Example 4: Comparison of Free Reagents for Acidity and Basicity

Carryover occurred when the Aβ peptide released using an acidic free reagent was measured by LC-MS/MS as in Example 3 above. Here, difference in the amount of Aβ peptide detected was compared between a case where a basic free reagent is used when releasing the Aβ peptide from the complex, and a case where an acidic free reagent is used when releasing the Aβ peptide, then replaced with a basic free reagent and subjected to LC-MS/MS.
(1) Sample Preparation As the Aβ peptide sample, the same Aβ40 peptide and Aβ42 peptide as in (1.3) of Example 1 were used, and a solution prepared so that the Aβ40 peptide was 50 pg/ml or 190 pg/ml in a 3% BSA solution, or a solution prepared so that the Aβ42 peptide was 26 pg/ml or 103 pg/ml in a 3% BSA solution was prepared and used. As the acidic free reagent, trifluoroacetic acid (TFA, FUJIFILM Wako Pure Chemical Corporation) and acetonitrile were mixed with pure water to prepare an acidic solution having a composition of 0.1% TFA and 30% acetonitrile. As the basic free reagent, a 1.68% ammonia and 50% acetonitrile solution was prepared in the same manner as in (1.4) of Example 1.

(2) Measurement
(2.1) Immunoprecipitation

An internal standard substance was added to each of the samples prepared in (1) above in the same manner as in (1.5) of Example 1, and magnetic particles immobilized with 6E10 antibody were added to form a complex.

(2.2) Elution of Aβ Peptide

Each complex prepared in (2.1) above was subjected to the same washing as in (1.6) of Example 1, and then 25 μL of the acidic free reagent or basic free reagent prepared in (1.1) above was added and mixed, and the mixture was allowed to stand for 1 minute. The magnetic particles were magnetically collected again, and supernatant was recovered as an eluate.

(2.3) Solvent Exchange

Of the eluates recovered in (2.2) above, the eluate obtained using the acidic free reagent was dried under reduced pressure for 1 hour under the conditions of a rotation speed of 1500 r/min and a temperature of 55° C. using Spin Dryer Standard VC-96R (TAITEC CORPORATION) in SpinDryer mode to volatilize the solvent. To a residue after drying under reduced pressure, 25 μL of the basic free reagent prepared in (1) above was added to resuspend the residue.

(2.4) Mass Spectrometry

The eluate (referred to as solution X) obtained by using each basic free reagent recovered in (2.2) above and the solution (referred to as solution Y) resuspended in (2.3) above were subjected to LC-MS/MS in the same manner as in (2) of Example 1, and MRM measurement was performed.

(3) Measurement Results

Figure 8A:
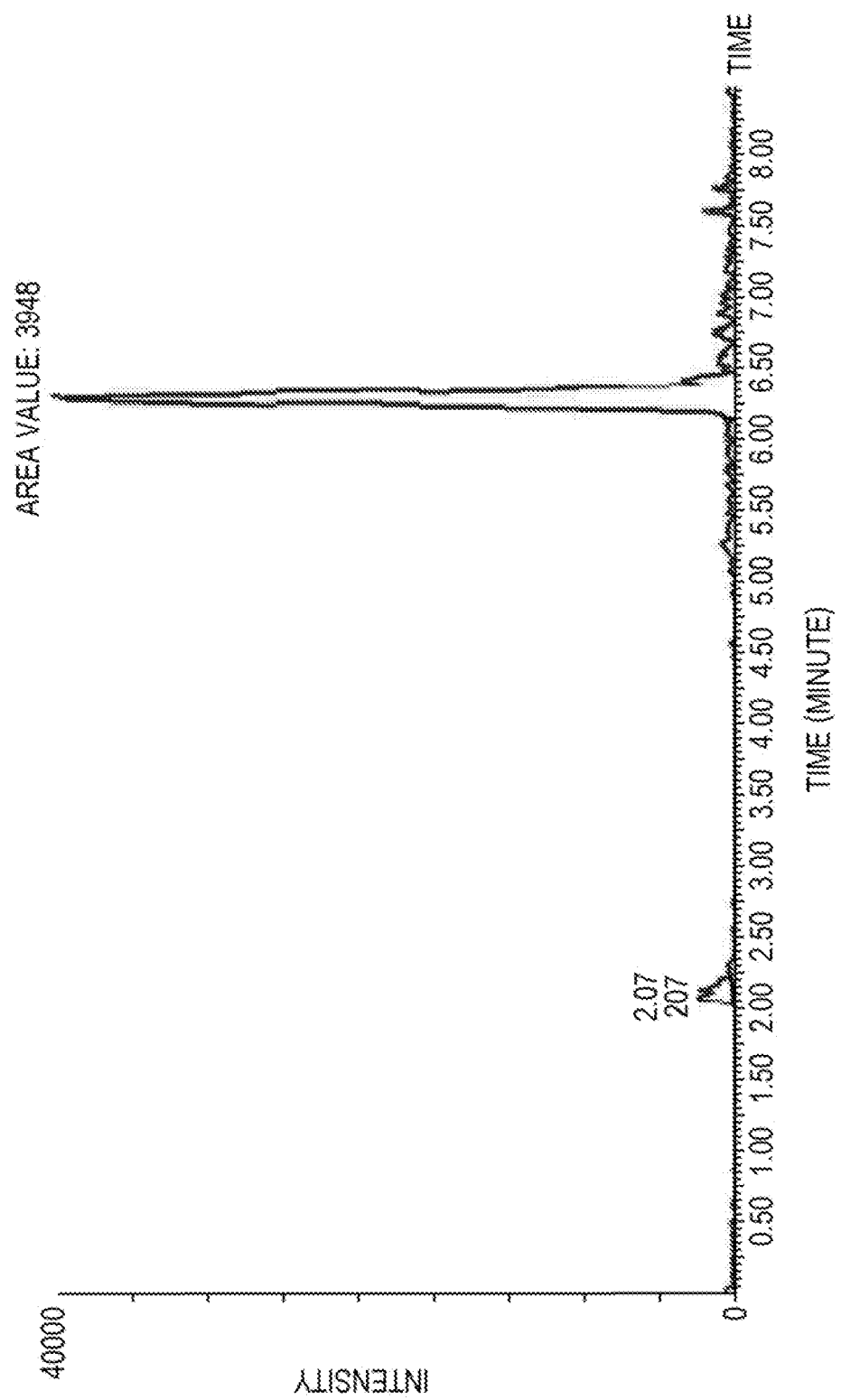
FIG. 8A is a diagram showing an amount of Aβ40 peptide when a 190 pg/ml Aβ40 peptide solution is eluted with a basic solution.
Figure 8B:
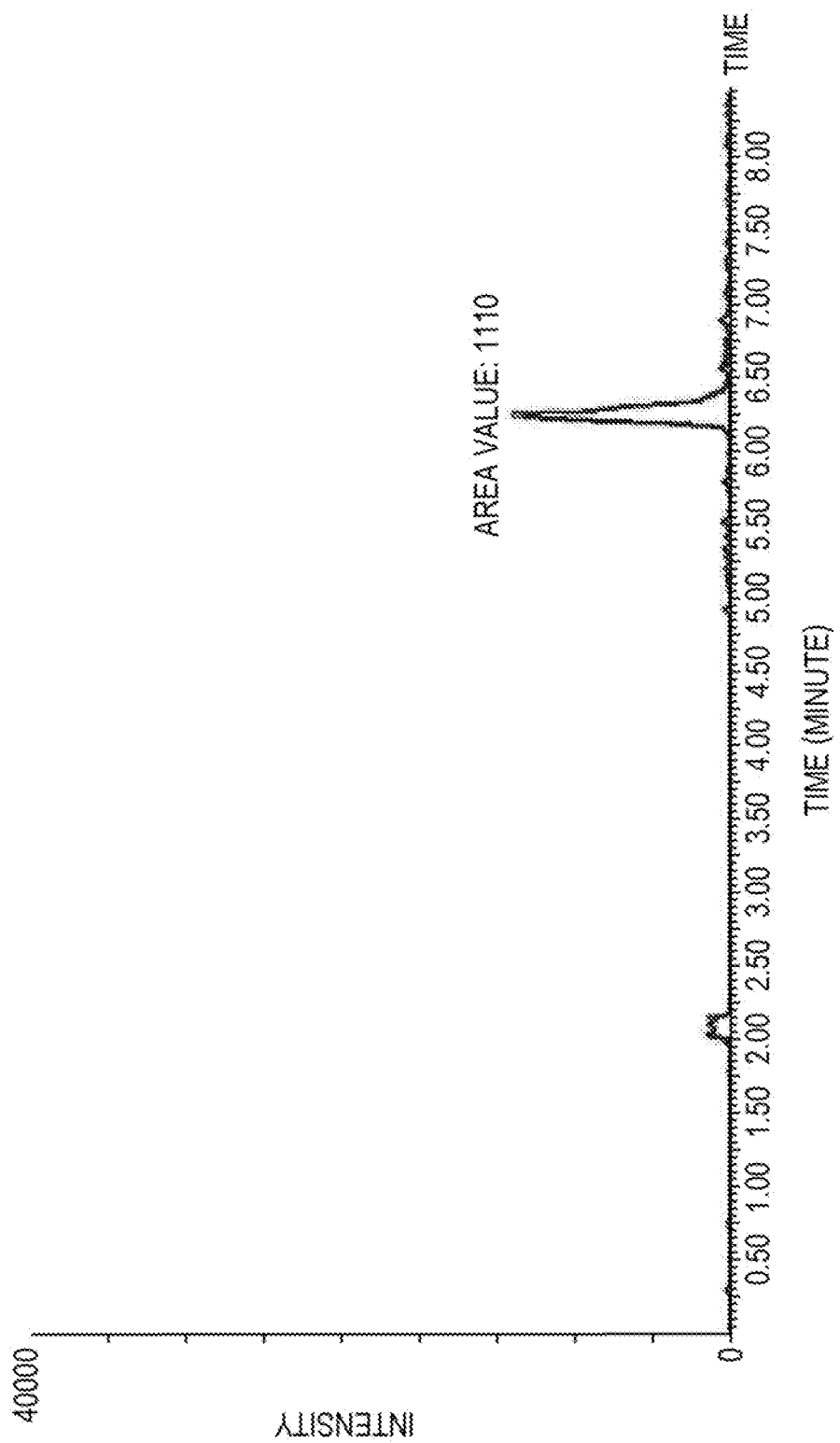
FIG. 8B is a diagram showing an amount of Aβ40 peptide when a 190 pg/ml Aβ40 peptide solution is eluted with an acidic solution.
Figure 8C:
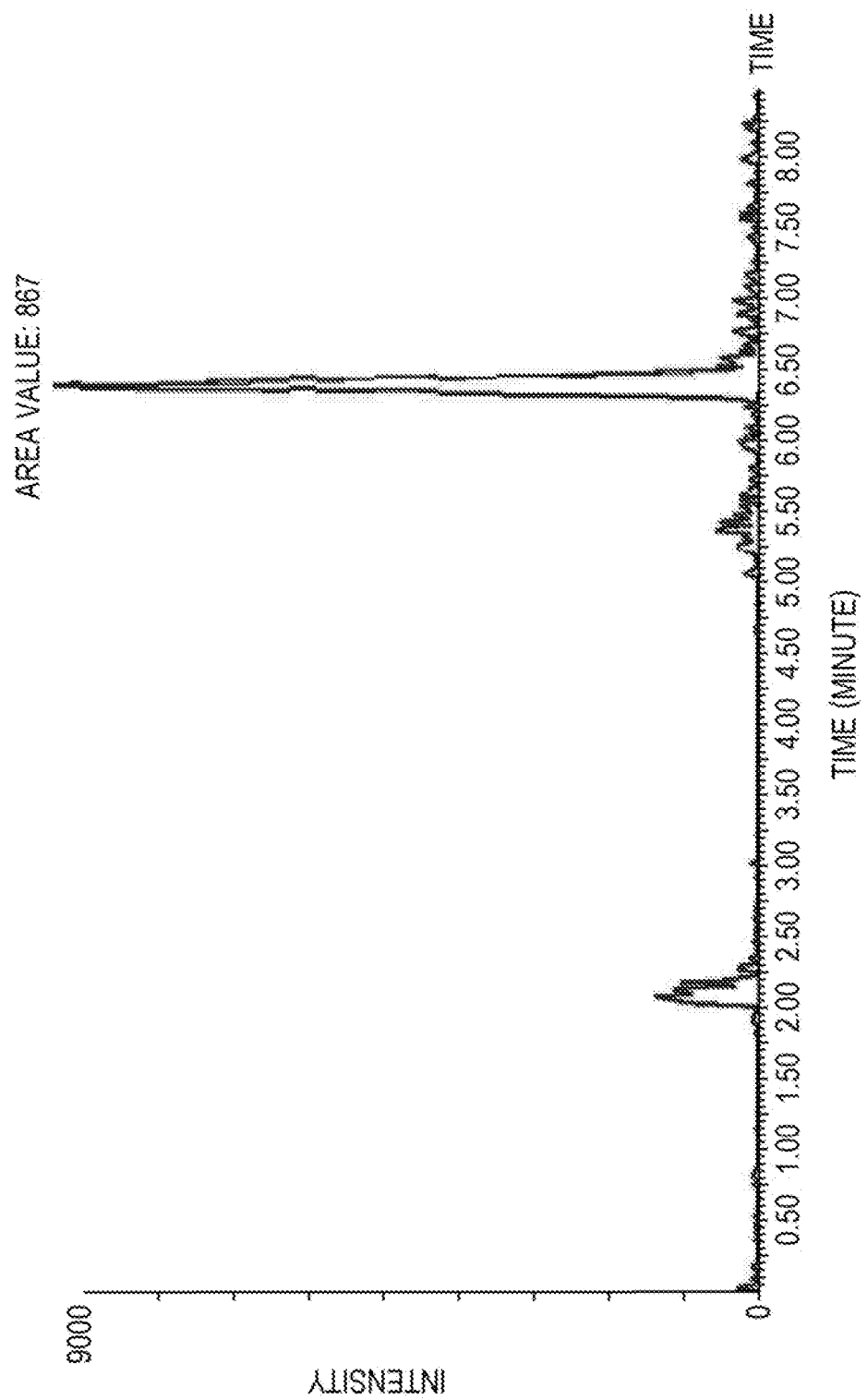
FIG. 8C is a diagram showing an amount of Aβ42 peptide when a 103 pg/ml Aβ42 peptide solution is eluted with a basic solution.
Figure 8D:
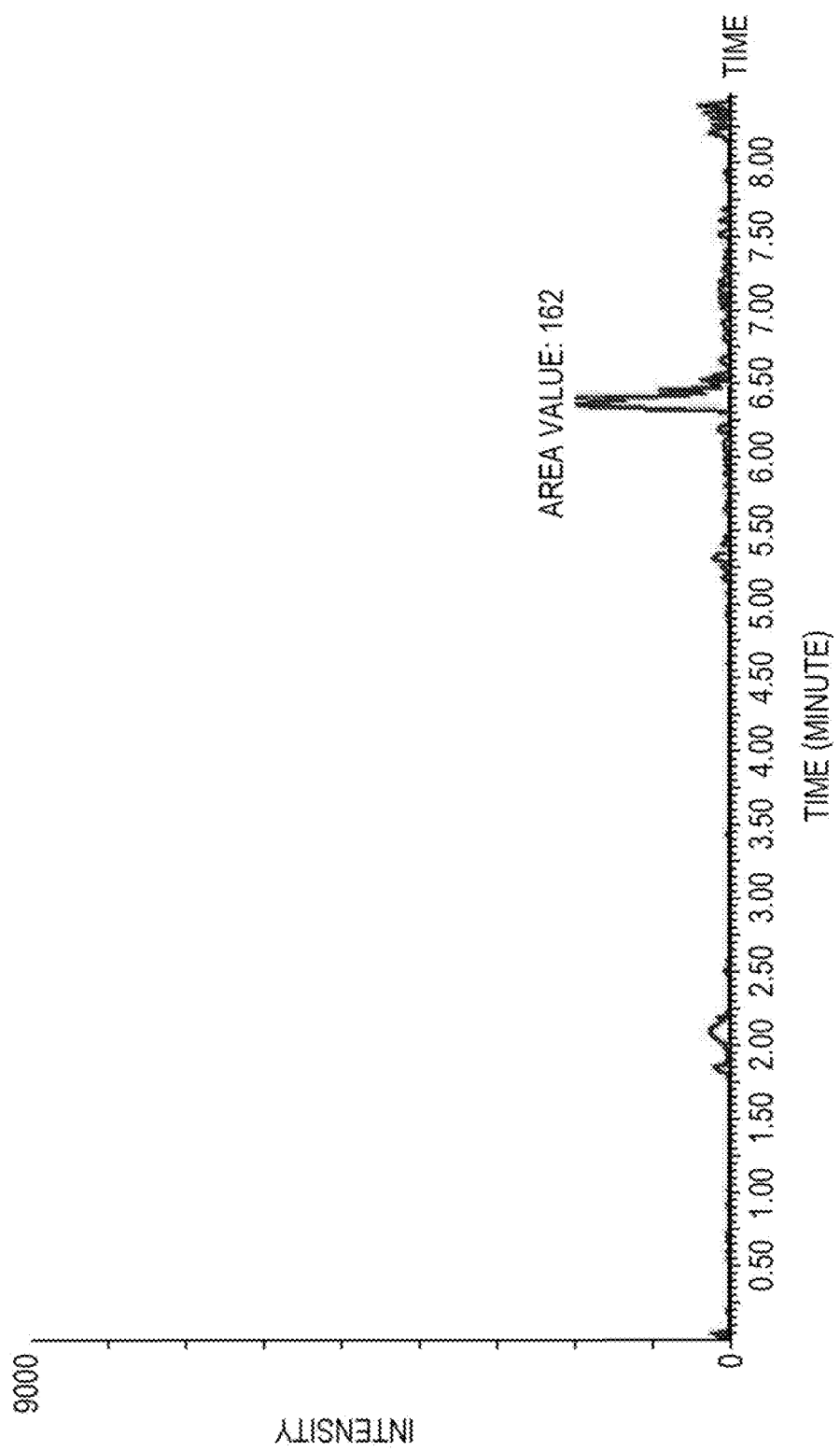
FIG. 8D is a diagram showing an amount of Aβ42 peptide when a 103 pg/ml Aβ42 peptide solution is eluted with an acidic solution.
Figure 9B:
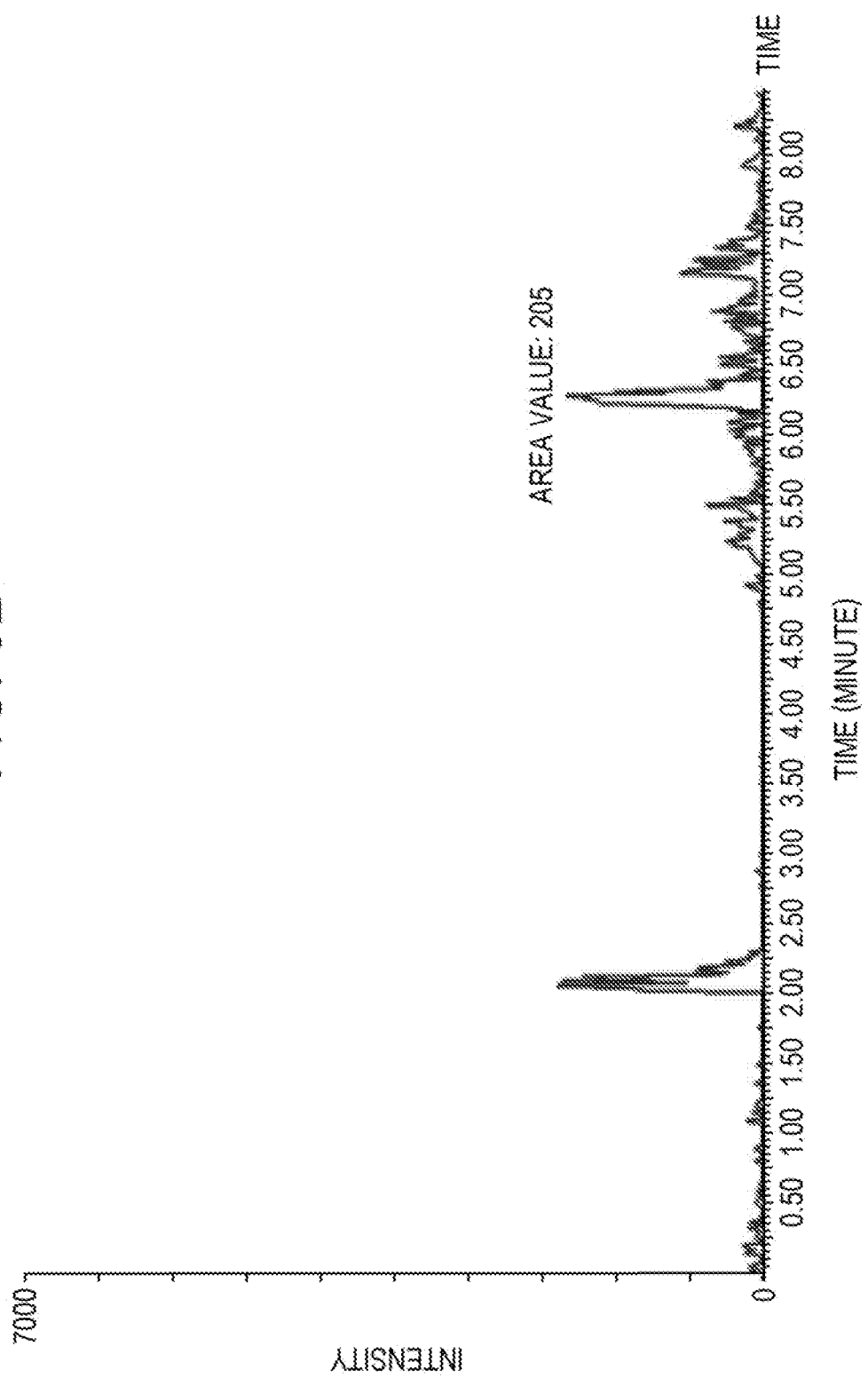
FIG. 9B is a diagram showing an amount of Aβ40 peptide when a 50 pg/ml Aβ40 peptide solution is eluted with an acidic solution.
Figure 9C:
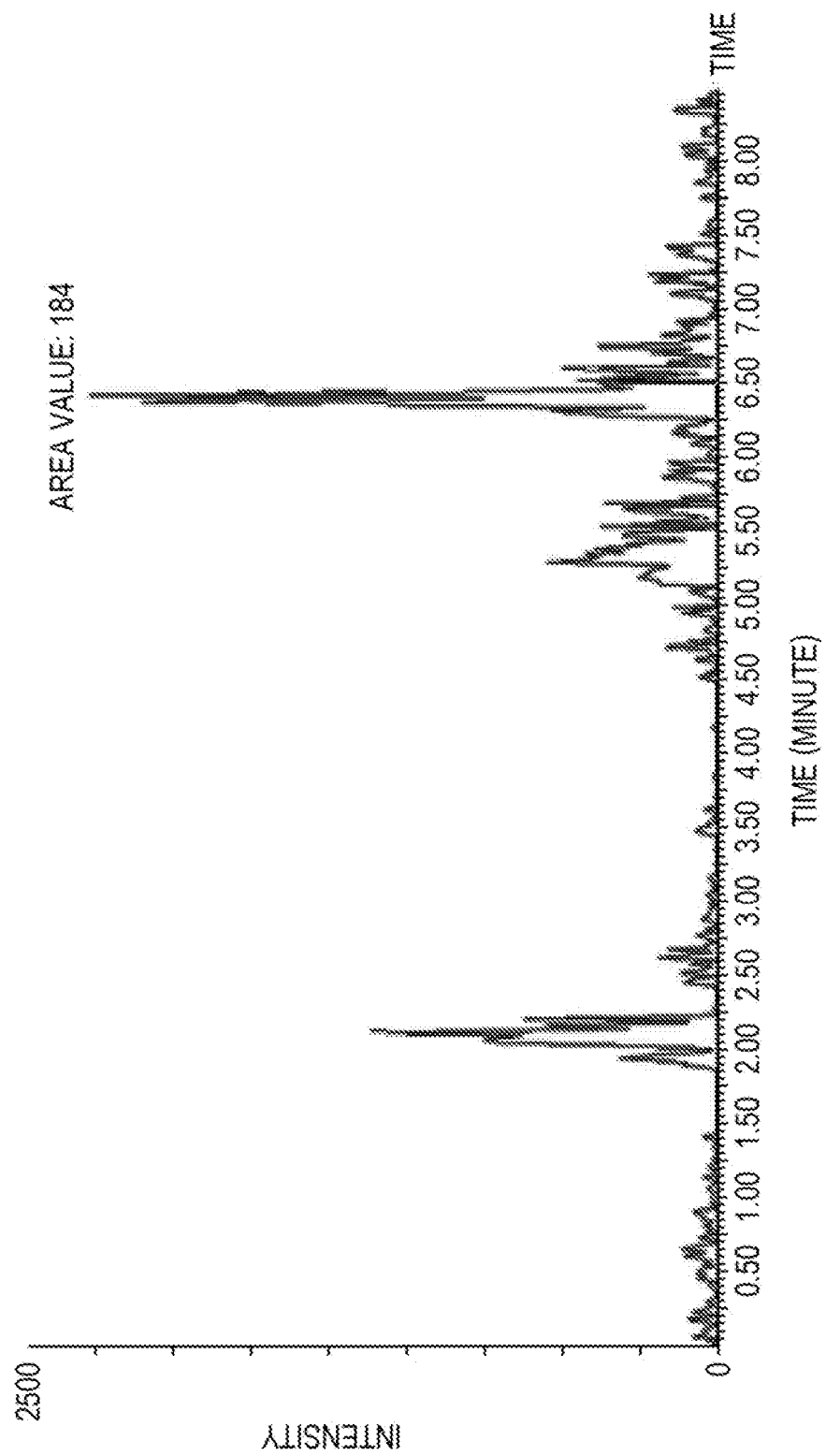
FIG. 9C is a diagram showing an amount of Aβ42 peptide when a 26 pg/ml Aβ42 peptide solution is eluted with a basic solution.
Figure 9D:
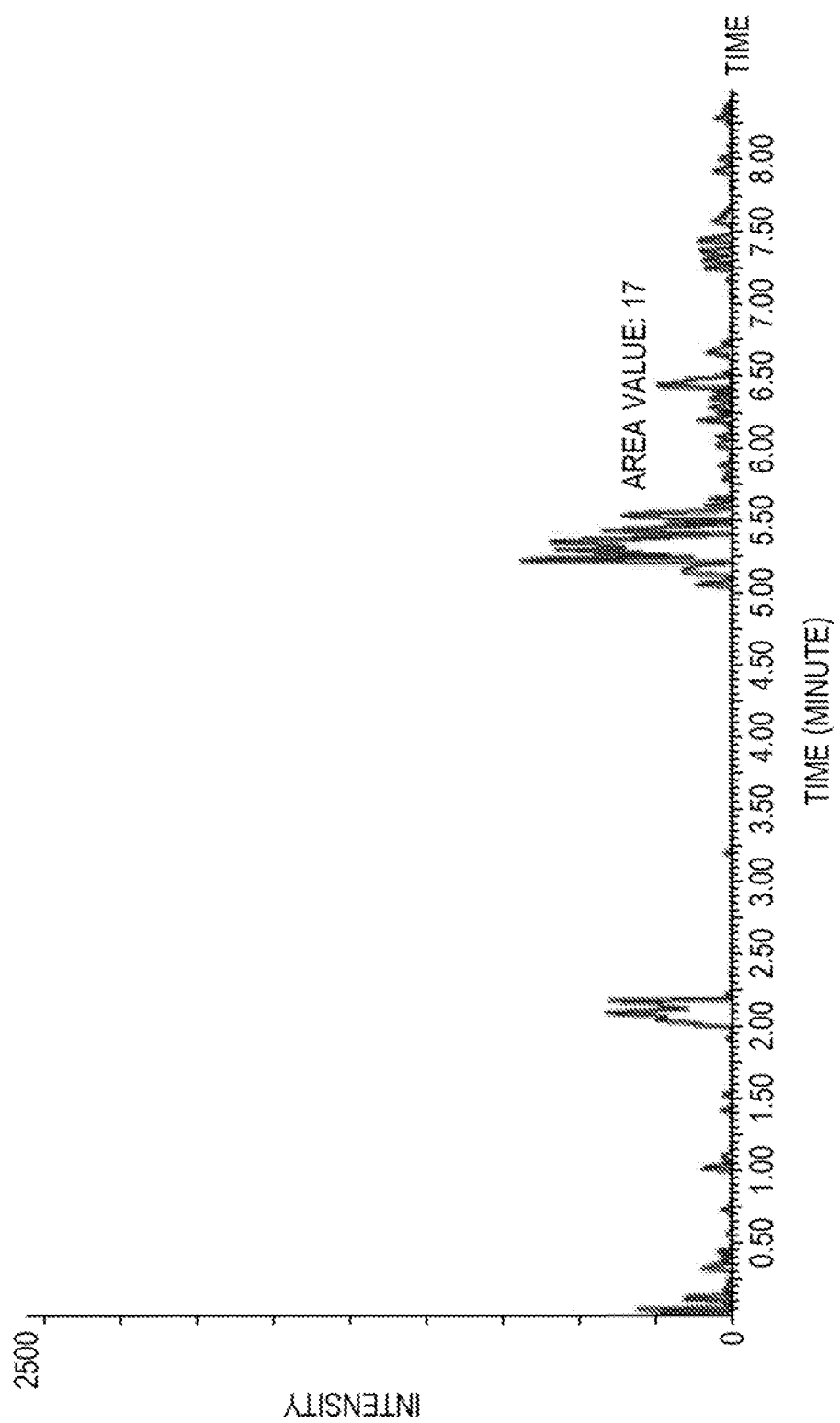
FIG. 9D is a diagram showing an amount of Aβ42 peptide when a 26 pg/ml Aβ42 peptide solution is eluted with an acidic solution.

Measurement results of solution A and solution B are shown in FIGS. 8A to 9D, respectively. FIG. 8A shows a measurement result of solution X using 190 pg/ml Aβ40 peptide, FIG. 8B shows a measurement result of solution Y using 190 pg/ml Aβ40 peptide, FIG. 8C shows a measurement result of solution X using 103 pg/ml Aβ42 peptide, FIG. 8D shows a measurement result of solution Y using 103 pg/ml Aβ42 peptide, FIG. 9A shows a measurement result of solution X using 50 pg/ml Aβ40 peptide, FIG. 9B shows a measurement result of solution Y using 50 pg/ml Aβ40 peptide, FIG. 9C shows a measurement result of solution X 26 pg/ml Aβ42 peptide, and FIG. 9D show a measurement result of solution Y using 26 pg/ml Aβ42 peptide. From these results, in the examples of Aβ peptides at all concentrations, the area value was larger when using the solution X than when using the solution Y. It was suggested that loss of Aβ peptide occurred when the process as described in (2.3) above was used in sample treatment.

What is claimed is:

1. A method for measuring an Aβ peptide, comprising:
mixing i) a blood sample comprising an Aβ peptide and ii) an antibody that specifically binds to the Aβ peptide, to form a complex of the Aβ peptide and the antibody;
releasing the Aβ peptide from the complex with a basic solution comprising acetonitrile and ammonia; and
measuring a released Aβ peptide in the basic solution by liquid chromatography-mass spectrometry,
wherein the basic solution containing the released Aβ peptide is used as is for liquid chromatography-mass spectrometry, and
wherein the basic solution has a pH of 11.4 or more.

2. The method according to claim 1, wherein the basic solution further comprises at least one selected from the group consisting of acetone, 1-propanol, 2-propanol, hexane, ethanol, dimethyl sulfoxide and methanol.

3. The method according to claim 1, wherein the antibody that specifically binds to the Aβ peptide is an antibody that binds to one or both of Aβ40 and Aβ42, and the Aβ peptide released from the complex in the releasing is at least one of Aβ40 and Aβ42, and a measured value of the at least one of Aβ40 and Aβ42 is acquired in the measuring.

4. The method according to claim 3, wherein the antibody that specifically binds to the Aβ peptide is an antibody that binds to both Aβ40 and Aβ42, and respective measured values of Aβ40 and Aβ42 are acquired in the measuring.

5. The method according to claim 1, wherein the antibody that specifically binds to the Aβ peptide is immobilized on a solid phase.

6. The method according to claim 1, wherein a reversed-phase column is used in the liquid chromatography-mass spectrometry.

7. The method according to claim 1, wherein the blood sample is mixed with a labeled internal standard substance, and in the measuring, a measured value of the AB peptide is acquired based on a measured value of the internal standard substance.

8. The method according to claim 7, wherein the internal standard substance is an Aβ peptide labeled with a stable isotope.

9. A method for measuring an Aβ peptide, comprising:
mixing i) a blood sample comprising an Aβ peptide and ii) an antibody that specifically binds to the Aβ peptide, to form a complex of the Aβ peptide and the antibody;
conducting bound/free separation to remove an unreacted free component that has not formed the complex and recover the complex;
releasing the Aβ peptide from the complex with a basic solution comprising acetonitrile and ammonia; and
measuring a released Aβ peptide in the basic solution by liquid chromatography-mass spectrometry,
wherein the basic solution containing the released Aβ peptide is used as is for liquid chromatography-mass spectrometry, and
wherein the basic solution has a pH of 11.4 or more.

10. The method according to claim 9, wherein the basic solution further comprises at least one selected from the group consisting of acetonitrile, acetone, 1-propanol, 2-propanol, hexane, ethanol, dimethyl sulfoxide and methanol.

11. A method for measuring an Aβ peptide, comprising:
mixing i) a blood sample comprising an Aβ peptide, ii) an antibody that specifically binds to the Aβ peptide and iii) a labeled internal standard substance, to form a complex of the Aβ peptide and the antibody and a complex of the labeled internal standard substance and the antibody, wherein the labeled internal standard substance is a labeled Aβ peptide;
conducting bound/free separation to remove an unreacted free component that has not formed the complex of the Aβ peptide and the antibody or the complex of the labeled internal standard substance and the antibody;
releasing with a basic solution comprising acetonitrile and ammonia the Aβ peptide from the complex of the Aβ peptide and the antibody, and releasing with the basic solution the labeled internal standard substance from the complex of the labeled internal standard substance and the antibody; and
measuring a released Aβ peptide and the labeled internal standard substance by liquid chromatography-mass spectrometry and quantifying the Aβ peptide based on a measured value of the labeled internal standard substance,
wherein the basic solution containing the released Aβ peptide is used as is for liquid chromatography-mass spectrometry, and
wherein the basic solution has a pH of 11.4 or more.

12. The method according to claim 11, wherein the basic solution further comprises at least one selected from the group consisting of acetonitrile, acetone, 1-propanol, 2-propanol, hexane, ethanol, dimethyl sulfoxide and methanol.

13. The method according to claim 11, wherein the internal standard substance is an Aβ peptide labeled with a stable isotope.

* * * * *